US008133491B1

(12) United States Patent
Selman et al.

(10) Patent No.: US 8,133,491 B1
(45) Date of Patent: Mar. 13, 2012

(54) COMPOSITIONS AND METHODS FOR TREATMENT OF HYPERPLASTIC DISORDERS

(75) Inventors: Steven H. Selman, Toledo, OH (US); Channing L. Hinman, Toledo, OH (US)

(73) Assignee: The University of Toledo, Toledo, OH (US)

( * ) Notice: Subject to any disclaimer, the term of this patent is extended or adjusted under 35 U.S.C. 154(b) by 13 days.

(21) Appl. No.: 12/696,600

(22) Filed: Jan. 29, 2010

Related U.S. Application Data

(60) Provisional application No. 61/148,601, filed on Jan. 30, 2009.

(51) Int. Cl.
*A61K 39/00* (2006.01)
(52) U.S. Cl. .................. 424/192.1; 514/19.2; 514/19.5; 514/21.1; 514/21.5; 530/327; 530/317
(58) Field of Classification Search .................. None
See application file for complete search history.

(56) References Cited

U.S. PATENT DOCUMENTS

| | | | |
|---|---|---|---|
| 5,116,615 A * | 5/1992 | Gokcen et al. | 424/94.2 |
| 6,365,164 B1 | 4/2002 | Schmidt | |
| 6,667,041 B2 | 12/2003 | Schmidt | |
| 7,001,602 B2 | 2/2006 | Schmidt | |
| 7,105,635 B2 | 9/2006 | Hinman et al. | |
| 7,153,514 B2 | 12/2006 | Schmidt | |
| 7,429,387 B2 | 9/2008 | Schmidt | |
| 2004/0120958 A1 * | 6/2004 | Bander et al. | 424/155.1 |
| 2004/0126380 A1 * | 7/2004 | Schmidt | 424/184.1 |

FOREIGN PATENT DOCUMENTS

WO WO 03005889 A2 * 1/2003

OTHER PUBLICATIONS

Modahl et al., Toxicon, 2010, vol. 55, pp. 612-618.*
Karlsson et al., Isolation of the Principal Neurotoxins of Two Naja naja Subspecies, Eur. J. Biochem. 21 (1971) 1-16.

* cited by examiner

*Primary Examiner* — Michael Szperka
(74) *Attorney, Agent, or Firm* — MacMillan, Sobanski & Todd, LLC

(57) ABSTRACT

A method for treating a subject includes injecting a therapeutic amount of a composition derived from a cobra toxin into a tissue of the subject in an amount sufficient to diminish at least one symptom of a hyperplastic disorder.

14 Claims, 15 Drawing Sheets

COMPOSITIONS AND METHODS FOR TREATMENT OF HYPERPLASTIC DISORDERS

CROSS-REFERENCE TO RELATED APPLICATIONS AND STATEMENT REGARDING SPONSORED RESEARCH

The present invention claims the benefit of the provisional patent application Ser. No. 61/148,601 filed Jan. 30, 2009. This invention was not made with any government support, and the government has no rights in this invention.

SEQUENCE LISTING

The instant application contains a Sequence Listing which has been submitted via EFS-web and is hereby incorporated by reference in its entirety. The ASCII copy, created on Mar. 24, 2010, is named 1-50754.txt, and is 7,651 bytes in size.

TECHNICAL FIELD

The present invention is directed to methods of treating conditions requiring removal or destruction of cellular elements, such as benign or malignant tumors in humans, using compounds based on peptides comprising amino acid sequences corresponding to, similar to or homologous to part of the amino acid sequence of cobra toxin proteins.

BACKGROUND OF THE INVENTION

There is no admission that the background art disclosed in this section legally constitutes prior art.

Benign prostatic hyperplasia (BPH) refers to the increase in size of the prostate in middle-aged and elderly men. It is characterized by hyperplasia of prostatic stromal and epithelial cells, resulting in the formation of large, fairly discrete nodules in the periurethral region of the prostate. When sufficiently large, the nodules compress the urethral canal to cause partial, or sometimes virtually complete, obstruction of the urethra which interferes with the normal flow of urine. It leads to symptoms of urinary hesitancy, frequent urination, increased risk of urinary tract infections and urinary retention. Adenomatous prostatic growth is believed to begin at approximately age 30 years.

The prostate gets larger in most men as they get older, and overall, 45% of men over the age of 46 can expect to suffer from the symptoms of BPH if they survive 30 years. Incidence rates increase from 3 cases per 1000 man—years at age 45-49 years, to 38 cases per 1000 man—years by the age of 75-79 years. Whereas prevalence rates are 2.7% for men aged 45-49, they increase to 24% by the age of 80 years. For some men, the symptoms may be severe enough to require treatment.

Thus, despite the growing body of knowledge regarding BPH, there is still a need to provide improved methods of treatment of BPH.

There remains a need in the art for new, less toxic treatments for treating unwanted cellular elements.

SUMMARY OF THE INVENTION

This invention is premised in part on the discovery that peptides containing amino acid sequences corresponding to part of the amino acid sequences of other cobra toxin proteins are capable of treating and/or killing unwanted cellular proliferations. These unwanted cellular proliferations include, but are not limited to, benign and malignant tumors, glandular (e.g., prostate) hyperplasia, and the like.

The present invention is directed to methods of treating unwanted cellular proliferations, (benign and malignant tumors, glandular (e.g., prostatic) hyperplasia, comprising administering to a subject in need thereof a therapeutically effective amount of a peptide comprising an amino acid sequence (or more than one sequence) corresponding to part of the amino acid sequence of a species of a cobra toxin protein.

Such peptides can be administered alone or conjugated to a carrier or an antibody. The peptides can be administered intraperitoneally, intratumorally, intralesionally, intradermally, topically, transdermally, via an injection, implantation device, sustained release system etc., either alone or conjugated to a carrier. Alternatively, the peptide can be expressed in vivo by administering a gene that expresses the peptide, by administering a vaccine that induces such production or by introducing cells, bacteria or viruses that express the peptide in vivo, because of genetic modification or otherwise.

In addition, the peptide may be used in conjunction with other therapies for treating benign and malignant tumors and other unwanted or harmful cellular growths.

In a first aspect, there is provided herein anti-hyperplasia peptide compositions comprising at least one synthetic analog of a first loop of a cobra venom cytotoxin, wherein the peptide is modified to increase the anti-hyperplasia activity of the peptide.

In certain embodiments, the peptide contains at least one hydrophobic amino acid, including tyrosine, as well as positively charged amino acids.

In certain embodiments, the peptide composition has a molecular mass less than 2000 Daltons and is cyclized by formation of a single disulfide bond, and wherein the structure of the peptide has no alpha helical components, but contains two apposed beta strands connected by a short string of amino acids.

In another aspect, there is provided a composition for inducing apoptosis in prostatic cells comprising at least one peptide having an amino acid sequence selected from the group consisting of SEQ ID NOs:1-18, or a physiologically acceptable salt thereof, the peptide being capable of causing cytotoxic activity.

In another aspect, there is provided an isolated peptide, wherein the peptide comprises one or more of SEQ ID NOs: 1-18 and can cause involution of a prostate as a result of glandular and/or stromal cell death.

In another aspect, there is provided an isolated, synthetic or recombinant peptide having the activity of causing granular and/or stromal cell death in prostatic tissue, wherein the peptide comprises at least one sequence represented by SEQ ID NOs:1-18, or derivatives thereof.

In another aspect, there is provided a pharmaceutical composition, comprising the peptide and a pharmaceutically acceptable carrier. In another aspect, there is provided a kit comprising the pharmaceutical composition in a vial.

In another aspect, there is provided a method to treat a subject having a hyperplastic disorder, comprising administering to the subject a therapeutically effective amount of the composition, wherein the hyperplastic disorder is alleviated. In certain embodiments, the subject is human.

In another aspect, there is provided a pharmaceutical composition for the treatment of a hyperplasia disorder comprising in a pharmaceutically effective amount at least one peptide derived from the venom of a cobra snake.

In another aspect, there is provided a pharmaceutical composition in which at least one peptide toxin is derived from the venom of a *naja naja atra* snake species.

In another aspect, there is provided an article of manufacture comprising a composition effective to a hyperplastic disorder and packaging material comprising a label which indicates that the composition can be used to treat the hyperplastic disorder, wherein said composition comprises a composition or a pharmaceutically acceptable salt or ester thereof.

In another aspect, there is provided use of a composition for treating hyperplasia in a subject, the composition comprising a cyclic peptide, 14 amino acids in length with a disulfide bond between residues 3 and 14 (Cys 3 and Cys 14) which consists of the following sequence: Leu-Lys-Cys-4-Lys-Leu-7-Pro-Leu-10-Tyr-Lys-Thr-Cys (SEQ ID NO: 20), where 4 is Asn or Gln; 7 is Val or Ile; 10 is Phe or Ala having one or more of the SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11 and SEQ ID NO:12.

In another aspect, there is provided use of a composition for treating hyperplasia in a subject, the composition comprising a cyclic peptide, 14 amino acids in length with a disulfide bond between residues 3 and 14 (Cys 3 and Cys 14) which consists of the following sequence: Leu-Lys-Cys-4-Lys-Leu-7-Pro-Leu-10-Tyr-Lys-Thr-Cys (SEQ ID NO: 21), where 4 is Asn or Gln; 7 is Val or Ile; 10 is Phe or Ala, having the SEQ ID NO:1, SEQ ID NO:2, SEQ ID NO:3, SEQ ID NO:4, SEQ ID NO:5, and SEQ ID NO:12, in which at least one amino acid is replaced with its corresponding D-amino acid.

In another aspect, there is provided a method for treating a subject with a prostatic disorder, the method comprising: injecting a therapeutic amount of a composition derived from a cobra toxin into a prostate gland of the subject patient, thereby alleviating a symptom of prostatic hyperplasia, benign prostatic hyperplasia or prostatic enlargement. In certain embodiments, the composition is derived from cobra toxin comprised of a *naja naja atra* venom or a derivative thereof.

In certain embodiments, the prostatic disorder comprises one or more of: prostatic hyperplasia, benign prostatic hyperplasia or prostatic enlargement.

In certain embodiments, the composition is administered in a pharmaceutically acceptable formulation selected from the group consisting of: a liquid, a powder, a cream, an emulsion, a suppository, a suspension, and a solution.

In certain embodiments, the composition is administered to the prostate of the patient by a route selected from the group consisting of: a single unilateral injection, serial unilateral injections and bilateral injections.

In certain embodiments, administration of the composition results in shrinkage of the prostate.

In another aspect, there is provided a method of treating a condition in a subject requiring removal or destruction of cells, the method comprising administering to the subject a therapeutically effective amount of a composition comprised of at least one peptide selected from one or more of SEQ ID NOs:1-18.

In certain embodiments, the composition is conjugated, linked, or bound to a molecule selected from the group consisting of: an antibody, antibody fragment, and an antibody-like binding molecule, wherein the molecule has a higher affinity for binding to a tumor or other target than binding to other cells.

In another aspect, there is provided a system for treating benign prostate hyperplasia (BPH) of a prostate, comprising: administering at least one composition comprising one or more peptides described in SEQ ID NOs:1-18 near a BPH tissue site of a subject in an amount sufficient to produce necrosis of cells of the BPH tissue site but insufficient to create damage to a majority of the BPH tissue site.

In another aspect, there is provided a method of treating a disease, disorder or condition in which inhibition of hyperplasia is beneficial in a subject suffering from a disease, disorder or condition in which such inhibition is beneficial, the method comprising: administering to the subject in need of such treatment a therapeutically effective amount of a compound comprised of at least one amino acid composition selected from SEQ ID NOs:1-12, a pharmaceutically acceptable salt thereof, and a pharmaceutically acceptable carrier, diluent or excipient.

Both the foregoing general description and the following detailed description are exemplary and explanatory and are intended to provide further explanation of the invention as claimed. Other objects, advantages, and features will be readily apparent to those skilled in the art from the following detailed description of the invention.

In a first aspect, there is provided herein a method of treatment for benign prostatic hyperplasia (BPH) which includes the direct injection of a therapeutic composition into the prostate. In particular, the therapeutic composition is comprised of cyclic anti-parallel beta-sheet peptide compositions that cause apoptosis in the prostate cells. The peptide compositions are useful to selectively kill cells The peptide compositions comprise at least one synthetic analog of the first loop of cobra venom cytotoxins/cardiotoxins. The peptide compositions contain hydrophobic amino acids, including tyrosine, as well as positively charged amino acids. The small peptide compositions have a molecular mass less than 2000 Daltons and are cyclized by the formation of a single disulfide bond. Their structure has no alpha helical components, but contains two apposed beta strands connected by a short string of amino acids. Examples of the peptide composition are described in the Hinman et al. U.S. Pat. No. 7,105,635 issued Sep. 12, 2006, to one of the co-inventors herein.

While not wishing to be bound by theory, the inventors herein now believe that the peptide compositions cause the atrophy and/or death of the stroma and glandular elements of the prostate, thereby causing a resultant decrease in the bulk of the prostate.

This application refers to various patents and publications. The contents of all of these are incorporated by reference. In addition, the following are incorporated herein by reference: Current Protocols in Molecular Biology, Current Protocols in Immunology, Current Protocols in Protein Science, and Current Protocols in Cell Biology, all John Wiley & Sons, N.Y., current edition; Sambrook, Russell, and Sambrook, Molecular Cloning: A Laboratory Manual, current edition, Cold Spring Harbor Laboratory Press, Cold Spring Harbor. In case of a conflict between the specification and a document incorporated by reference, the specification shall control. The determination of whether a conflict or inconsistency exists is within the discretion of the inventors and can be made at any time.

BRIEF DESCRIPTION OF THE DRAWINGS

FIG. 1 contains photographs of rat prostate injected with a peptide composition, as described herein, toxin showing atrophy of the injected pro static lobes.

FIG. 2 contains histology photographs of one of the rat prostates injected with cobra toxin showing atrophy of the injected prostatic lobe.

DETAILED DESCRIPTION OF THE PREFERRED EMBODIMENT(S)

Figure 1:
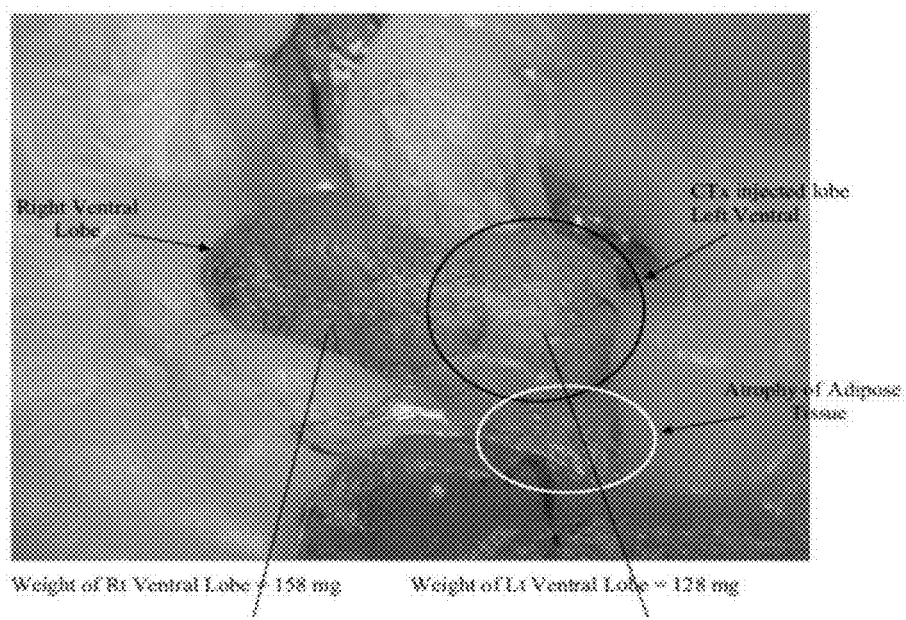

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

Before the present proteins, nucleotide sequences, peptides, etc., and methods are described, it is understood that this invention is not limited to the particular methodology, protocols, cell lines, vectors, and reagents described, as these may vary. It also is to be understood that the terminology used herein is for the purpose of describing particular embodiments only, and is not intended to limit the scope of the present invention which will be limited only by the appended claims.

Terms and phrases used herein are defined as set forth below unless otherwise specified.

Throughout this description, the singular forms "a," "an," and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

"Cobra toxin peptides" refers to at least one peptide comprising at least one fragment or subsequence of at least one of the peptide SEQ ID NOs:1-18, and includes any homologue, fragment, derivative, variant, fusion protein, and peptide mimetics of the peptide unless the context indicates otherwise. The expression "cobra toxin peptides" includes (but is not limited to) peptides comprising at least one peptide selected from the group consisting of: SEQ ID NOs:1-18.

"Composition" as used herein, refers broadly to any composition containing a recited peptide or amino acid sequence. The composition may comprise a dry formulation, an aqueous solution, or a sterile composition.

"Fragment" or "subsequence" refers to a protein or polypeptide that consists of a continuous subsequence of the amino acid sequence of a protein or peptide and includes naturally occurring fragments such as splice variants and fragments resulting from naturally occurring in vivo protease activity. Such a fragment may be truncated at the amino terminus, the carboxy terminus, and/or internally (such as by natural splicing). Such fragments may be prepared with or without an amino terminal methionine. The term "fragment" includes fragments, whether identical or different, from the same protein or peptide, with a contiguous amino acid sequence in common or not, joined together, either directly or through a linker. As a consequence, any peptide that includes a fragment of, for example, SEQ ID NO:1, can be any of those selected above, as well as other fragments or subsequences that, while not delineated herein for purposes of brevity, will be readily apparent to those skilled in the art. The skilled artisan also will be capable of selecting a suitable fragment for use in the embodiments without undue experimentation using the guidelines and procedures outlined herein.

The term "variant" refers to a protein or polypeptide in which one or more amino acid substitutions, deletions, and/or insertions are present as compared to the amino acid sequence of a protein or peptide and includes naturally occurring allelic variants or alternative splice variants of a protein or peptide. The term "variant" includes the replacement of one or more amino acids in a peptide sequence with a similar or homologous amino acid(s) or a dissimilar amino acid(s). There are many scales on which amino acids can be ranked as similar or homologous. Preferred variants and/or preferred substitutions include conservative substitutions that have little or no effect on the overall net charge, polarity, or hydrophobicity of the protein.

Other variants can consist of less conservative amino acid substitutions, such as selecting residues that differ more significantly in their effect on maintaining the structure of the polypeptide backbone in the area of the substitution, for example, as a sheet or helical conformation; the charge or hydrophobicity of the molecule at the target site; or, the bulk of the side chain. The term "variant" also encompasses polypeptides that have the amino acid sequence of a cobra toxin peptide with at least one and up to 25 or more additional amino acids flanking either the N-terminal or C-terminal of the Peptide.

"Derivative" refers to a chemically modified protein or polypeptide that has been chemically modified either by natural processes, such as processing and other post-translational modifications, but also by chemical modification techniques, as for example, by addition of one or more polyethylene glycol molecules, sugars, phosphates, and/or other such molecules, where the molecule or molecules are not naturally attached to the wild-type cobra toxin proteins. Derivatives include salts. Such chemical modifications are well described in basic texts, as well as in research literature, and they are well known to those of skill in the art. It will be appreciated that the same type of modification may be present in the same or varying degree at several sites in a given protein or polypeptide.

"Hyperplasia" refers to an increase in the volume of a tissue or organ caused by an increase in the number of cells, typically due to cell proliferation.

"Hypertrophy" refers to an increase in the volume and/or mass of a tissue or organ. In most cases, the increase is caused at least in part by an increase in cell number (hyperplasia), an increase in cell size, or both. Hypertrophy may also be caused by or may involve deposition or collection of noncellular material such as lipid, extracellular matrix components such as collagen and proteoglycans, etc.

"Liposomes" are artificial microscopic spherical particles formed by a lipid bilayer (or multilayers) enclosing an aqueous compartment. Liposomes are commonly used in molecular biology and medicine as a delivery vehicle for various types of molecules (such as proteins, small molecules, DNA, and RNA), including a number of different drugs and can be used for delivering the compositions of the invention.

"Local delivery," in reference to delivery of a composition or device of the invention containing a therapeutic agent, refers to delivery that does not rely primarily upon transport of the agent to its intended target (cells, tissue, or organ) via the vascular system. The agent is delivered directly to its intended target or in the vicinity thereof, e.g., by injection or implantation of the composition or device containing the agent. Following local administration in the vicinity of a target site, the agent may diffuse to the intended target. If a composition or device is injected or implanted in the vicinity of a target tissue rather than directly into the target tissue, the distance between the site of injection or implantation will be selected so as to allow diffusion of the therapeutic agent to the target in effective amounts. Typically, "in the vicinity" or "near" refers to locations within several centimeters or less (e.g., within 3-4 cm), typically 1 cm or less of at least a portion of a target tissue or organ. It will be understood that once having been locally delivered, a fraction of a therapeutic agent (typically only a minor fraction of the administered dose) may enter the vascular system and be transported to another location, including to its intended target.

A variety of different types of compositions can be delivered locally. In certain embodiments of the invention the composition comprises a liquid. A liquid composition can comprise a therapeutic agent dissolved, suspended, or dispersed therein. The therapeutic agent may be a nucleic acid, small molecule, protein, etc. Liquid compositions can comprise polymer/nucleic acid complexes. Liquid compositions can comprise solid nanoparticles or microparticles comprising a therapeutic agent. Local delivery of a liquid composition may be accomplished in a number of different ways that are known in the art. For example, a liquid composition may be injected directly into its intended target tissue or in the vicinity thereof. The composition may be delivered by needle and syringe, catheter, cannula, etc. The composition may be delivered during laparoscopy and/or using ultrasound guidance or other imaging guidance. A liquid composition can also be administered locally to its intended target tissue during surgery, in which case it can be delivered using a syringe or poured from a suitable vessel. Alternately, a material can be wetted with the composition and then used to apply the liquid composition to an area of tissue.

In certain embodiments, the composition comprises a gel or forms a gel following local administration. Gels can be delivered locally, e.g., either by injection or by application to the target tissue, e.g., during surgery. Gels may be delivered as liquid compositions containing a material that forms a gel following introduction into the body. A solution containing the gel-forming material and a therapeutic agent may be prepared by combining the gel-forming material and therapeutic agent in solution using any suitable method, e.g., by adding the therapeutic agent to a solution containing the gel-forming material.

In certain embodiments the composition forms a gel following introduction into the body, e.g., upon contact with a physiological fluid. The composition may also be capable of forming a gel upon contact with a fluid such as phosphate buffered saline, or other fluid containing appropriate ions. Thus the composition can be injected at an appropriate location, e.g., in the vicinity of a target tissue where it forms a gel.

Alternately, a preshaped gel implant can be made, e.g., by introducing the solution into a mold or cavity of the desired shape and allowing gel formation to occur in the presence of a suitable concentration of a salt. The salt can be added either prior to or following the introduction of the solution into the mold or cavity. The mold or cavity can be, e.g., any structure that contains a hollow space or concave depression into which a solution can be introduced. In another embodiment, a film or membrane is formed from the gel-forming solution containing a therapeutic agent.

Release of the agent from the gel can occur by any mechanism, e.g., by diffusion of the agent out of the gel, as a result of breakdown of the gel, or both. In certain embodiments of the invention the gel-forming material also comprises at least some solid material in addition to soluble material, which may modulate the rate of release of the therapeutic agent.

A variety of different gel-forming materials can be used in the present invention. Preferably the gel is a hydrogel, by which is meant a gel that contains a substantial amount of water. Preferably the material and the gel that it forms are biocompatible. Preferably the material and the gel that it forms are biodegradable.

For treatment of BPH, a therapeutic composition in substantially liquid form can be injected into the prostate gland using a number of different routes known in the art including transperineal, transrectal, or transurethral. For transurethral injection, a curved needle may be used.

In certain embodiments, the composition may be a drug delivery device comprising a solid material such as polymeric matrix impregnated with, or encapsulating, a therapeutic agent. The device may be shaped as a rod, disk, wafer, tube, sheet, or the like. The device is implanted into the body at the location of the target tissue or in the vicinity thereof, e.g., using conventional surgical techniques. For example, the device may be implanted into the prostate gland. Solid microparticles or nanoparticles, preferably biodegradable, comprising a therapeutic agent can also be implanted. The microparticles or nanoparticles may be contained within a second polymeric matrix or other drug delivery device. The therapeutic agent is typically released from the polymer over a period of time, e.g. by diffusion out of the matrix or release into the extracellular environment as the matrix degrades or erodes.

"Operably linked", or operably associated, refers to a relationship between two nucleic acid sequences wherein the expression of one of the nucleic acid sequences is controlled by, regulated by, modulated by, etc., the other nucleic acid sequences, or a relationship between two polypeptides wherein the expression of one of the polypeptides is controlled by, regulated by, modulated by, etc., the other polypeptide. For example, the transcription of a nucleic acid sequence is directed by an operably linked promoter sequence; post-transcriptional processing of a nucleic acid is directed by an operably linked processing sequence; the translation of a nucleic acid sequence is directed by an operably linked translational regulatory sequence; the transport, stability, or localization of a nucleic acid or polypeptide is directed by an operably linked transport or localization sequence; and the post-translational processing of a polypeptide is directed by an operably linked processing sequence. Preferably a nucleic acid sequence that is operably linked to a second nucleic acid sequence, or a polypeptide that is operably linked to a second polypeptide, is covalently linked, either directly or indirectly, to such a sequence, although any effective three-dimensional association is acceptable.

"Polynucleotide", or oligonucleotide, refers to a polymer of nucleotides. A polynucleotide may be provided by a variety of means known in the art. In certain embodiments, the polynucleotide has been engineered using recombinant techniques (for example, see Ausubel et al. Current Protocols in Molecular Biology (John Wiley & Sons, Inc., New York, 1999); Molecular Cloning: A Laboratory Manual, 2nd Ed. by Sambrook, Fritsch, and Maniatis (Cold Spring Harbor Laboratory Press: 1989). A polynucleotide may also be obtained from natural sources and purified from contaminating components found normally in nature. The polynucleotide may be synthesized using enzymatic techniques, either within cells or in vitro. A polynucleotide may be chemically synthesized, e.g., using standard solid phase chemistry. A polynucleotide may be modified by chemical and/or biological means. In certain embodiments, these modifications lead to increased stability of the polynucleotide. Modifications include methylation, phosphorylation, end-capping, etc.

"Polynucleotide sequence" or "nucleic acid sequence" can refer to the nucleic acid material itself and is not restricted to the sequence information (i.e., the succession of letters chosen among the five base letters A, G, C, T, or U) that biochemically characterizes a specific nucleic acid, e.g., a DNA or RNA molecule. A nucleic acid sequence is presented in the 5' to 3' direction unless otherwise indicated.

"Polypeptide" can refer to a polymer of amino acids. A protein is a molecule composed of one or more polypeptides. A peptide is a relatively short polypeptide, typically between about 2 and 60 amino acids in length. The terms "protein", "polypeptide", and "peptide" may be used interchangeably. Polypeptides used herein typically contain amino acids such as those that are naturally found in proteins. However, amino acids that are not naturally found in proteins (i.e., amino acids that either do or do not occur in nature and that can be incorporated into a polypeptide chain), and/or amino acid analogs can also or alternatively be used. One or more of the amino acids in a polypeptide may be modified, for example, by the addition of a chemical entity such as a carbohydrate group, a phosphate group, a farnesyl group, an isofarnesyl group, a fatty acid group, a linker for conjugation, functionalization, or other modification, etc. Modifications may include cyclization of the peptide, the incorporation of D-amino acids, etc. Preferably the modification does not substantially interfere with the desired biological activity of the polypeptide.

Polypeptides of use in this invention may, for example, be purified from natural sources, produced in vitro or in vivo in suitable expression systems using recombinant DNA technology in suitable expression systems (e.g., by recombinant host cells or in transgenic animals or plants), synthesized through chemical means such as conventional solid phase peptide synthesis and/or using methods involving chemical ligation of synthesized peptides.

Polypeptide sequence and amino acid sequence can refer to the polypeptide material itself and is not restricted to the sequence information (i.e., the succession of letters or three letter codes chosen among the letters and codes used as abbreviations for amino acid names) that biochemically characterizes a polypeptide. A polypeptide sequence presented herein is presented in an N-terminal to C-terminal direction unless otherwise indicated.

"Subject" refers to an individual to whom an agent is to be delivered, e.g., for experimental, diagnostic, and/or therapeutic purposes. Preferred subjects are mammals, particularly domesticated mammals (e.g., dogs, cats, etc.), primates, or humans.

"Target cell, tissue, or organ" is a cell, tissue, or organ to which a composition of the invention is to be delivered and/or in which the composition or an agent contained in the composition is to be active. Typically a target tissue or organ is one whose size (i.e., the value of one or more dimension) and/or volume is to be reduced or whose continued increase in size and/or volume is to be inhibited or prevented. If the reduction or inhibition of continued increase in size and/or volume takes place by reducing the number and/or proliferation of one or more cell types in a target tissue or organ, the cell type(s) is considered to be a target cell.

"Therapeutic agent" refers to an agent (e.g., a polynucleotide, polypeptide, or small molecule) that is administered to a subject to treat a disease, disorder, or other clinically recognized condition that is harmful or undesirable to the subject, or for prophylactic purposes. The term "therapeutic agent" includes polynucleotides that encode therapeutic polypeptides, e.g., cytotoxic or cytostatic polypeptides such as those described herein.

"Tissue growth" refers to an expansion or increase in at least one dimension of the tissue, typically resulting in an expansion or increase in the total volume of the tissue, relative to a previous state (e.g., a normal state) or relative to a desired state. The growth is typically due at least in part to proliferation of one or more cell types in the tissue (hyperplasia) or may be due at least in part to other causes of hypertrophy. In certain instances the dimensions of the tissue may fall within the normal range for the general population or may be considered normal given the subject's other physical characteristics (e.g., height, weight, sex), but may cause symptoms and/or be displeasing to the subject. The tissue growth may simply be an increase in size associated with normal growth, e.g., growth to adulthood and may not be due to any specific disease process.

"Treating" refers to providing treatment, i.e., providing any type of medical and/or surgical management of a subject. The treatment can be provided in order to reverse, alleviate, inhibit the progression of, prevent or reduce the likelihood of a disease or condition, or in order to reverse, alleviate, inhibit or prevent the progression of, prevent or reduce the likelihood of one or more symptoms or manifestations of a disease or condition.

"Preventing" refers to causing a disease or condition, or symptom or manifestation of such not to occur. Treating can include administering a composition or device of this invention to the subject following the development of one or more symptoms or manifestations indicative of a disease or condition such as BPH, e.g., in order to reverse, alleviate, reduce the severity of, and/or inhibit or prevent the progression of the condition and/or to reverse, alleviate, reduce the severity of, and/or inhibit or prevent the progression of one or more symptoms or manifestations of the disease or condition. A composition or device of this invention can be administered to a subject who has developed a disease or condition such as BPH or is at increased risk of developing such a disorder relative to a member of the general population that would normally be considered susceptible to developing the disorder (e.g., males in the case of BPH).

A composition or device of this invention can be administered prophylactically, i.e., before development of any symptom or manifestation of the disease or condition. Typically in this case the subject will be at increased risk of developing the disease or condition relative to a member of the general population that would normally be considered susceptible to developing the disorder.

"Tumor" refers to an abnormal mass or lump of tissue, typically caused by excessive cell division. Tumors can be benign (non-cancerous) or malignant (cancerous). Benign and malignant tumors are typically distinguished on the basis of their clinical features and/or based on histopathology, cytogenetic features, immunological features, gene expression profile, etc. A benign tumor remains confined to a local area, typically within a fibrous capsule that separates it from surrounding normal tissue. Benign tumors generally do not infiltrate or invade adjacent tissues or spread to distant locations within the body (metastasize), and generally are not fatal. A malignant tumor (cancer), typically spreads locally and/or to remote sites within the body, and is frequently fatal if untreated. Malignant tumors (cancers) are often poorly differentiated and frequently display variation in cell size and shape.

"Vector" refers to a nucleic acid or a virus or portion thereof (e.g., a viral capsid) capable of mediating entry of, e.g., transferring, transporting, etc., a nucleic acid molecule into a cell.

The invention provides compositions and methods for treating a disease or condition characterized by inappropriate or excessive noncancerous tissue growth. The compositions comprise a tissue-selective or tissue-specific therapeutic agent, a tissue-selective or tissue-specific delivery vehicle, or both. The methods comprise administering a tissue-selective or tissue-specific therapeutic composition to the subject in an amount effective to cause a reduction in the size of the tissue and/or to inhibit or prevent continued increase in size of the tissue.

By "reduction in size" is meant a decrease in the value of one or more dimensions of the tissue, typically resulting in a decrease in total volume of the tissue. If the target tissue is present in an organ, the volume of the organ will be reduced and/or continued increase in volume of the organ will be inhibited or prevented.

By "increase in size" is meant an increase in the value of one or more dimensions of the tissue, typically resulting in an increase in total volume of the tissue.

By "tissue-selective" is meant that the composition acts on the tissue whose size is to be reduced while having no effect, or significantly less effect, on at least one other tissue type, e.g., one, several, or many other tissue types (i.e., nontarget tissue types).

By "tissue-specific" is meant that the composition acts on the tissue whose size is to be reduced while having no effect, or significantly less effect, on most or all other tissue types (i.e., nontarget tissue types).

In certain embodiments of the invention an effective composition reduces at least one dimension or, preferably, the volume of the target tissue, or an organ in which the target tissue is present, to between 0% and 95% of its initial value, e.g., to 5% or less, 10% or less, 20% or less, 30% or less, 40% or less, 50% or less, 60% or less, 70% or less, 80% or less, or 90% or less, or 95% or less of its initial value. Preferably an effective composition reduces the volume of a target tissue or organ in which the target tissue is present to 75% or less of its initial volume. Typically a reduction in volume will be accompanied by a reduction in wet and/or dry weight of the target tissue, organ, etc. The reduction in weight may be greater than, less than, or approximately the same as the reduction in volume on a percentage basis.

For purposes of description it will be assumed that the relevant parameter is volume, but the same considerations apply to size as determined by the value of one or more dimensions of the tissue or organ. The dimension can be, e.g., length, width, depth, diameter, or distance between any two points on a two-dimensional projection of the tissue or organ.

A tissue-selective or tissue-specific composition may cause some reduction in the volume of a nontarget tissue, but the magnitude of the reduction is less.

Tissue selectivity and/or specificity may be conferred by at least four different approaches, one or more of which is used in each of the various embodiments of the invention. One such approach is the use of local delivery.

In certain embodiments, a cell type selective or cell type specific delivery vehicle can also be used. A delivery vehicle is an agent that is typically not itself effective by itself to reduce the size of the tissue but that is present within a therapeutic composition and serves one or more of the following purposes. A delivery vehicle may enhance delivery of the therapeutic agent to cells or to a site within the body, e.g., by enhancing cell uptake or appropriate distribution of the therapeutic agent inside cells. A delivery vehicle may control or modulate bioavailability of the therapeutic agent, e.g., bioavailability may be controlled or modulated by the time course of release of the therapeutic agent from the vehicle. A delivery vehicle may stabilize the therapeutic agent (e.g., protect it from degradation), inhibit its uptake by nontarget cells (e.g., macrophages), inhibit its excretion, etc. A cell type selective or cell type specific delivery vehicle preferably selectively enhances delivery of the therapeutic agent to cells or tissues of particular type(s), selectively stabilizes the therapeutic agent in cells or tissues of particular type(s), and/or selectively controls or modulates release or distribution of the therapeutic agent within cells or tissues of particular type(s). A delivery vehicle is therefore distinct from commonly used pharmaceutical ingredients such as diluents or excipients that serve as bulking agents or fillers.

Another approach is to use a delivery vehicle that is specifically targeted to a cell type of interest, e.g., a cell type that is prevalent within the tissue whose size is to be reduced While the compositions and methods of the invention are of use in treating a wide variety of diseases and conditions associated with excessive or inappropriate tissue growth, one application of particular interest is the treatment of benign prostatic hyperplasia (BPH), sometimes referred to as benign prostatic hypertrophy. BPH will be taken as a representative context in which to describe certain of the inventive compositions and methods for treatment of hypertrophic tissues. The following section provides information on BPH, following which embodiments of the invention that employ one or more of the approaches described herein with particular reference to treatment of BPH.

Example—Benign Prostatic Hyperplasia

This disclosure is premised, in part, on the discovery that certain peptides, including specific peptides described by the amino acid sequences SEQ ID Nos:1-12, are capable of treating and/or killing unwanted cellular proliferations. These unwanted cellular proliferations include, but are not limited to benign and malignant tumors, glandular (e.g. prostate) hyperplasia.

The embodiments described herein are premised in part on the surprising and unexpected discovery that certain peptide fragments and subsequences of these "cobra toxin" peptide compositions also have the capability of treating and/or killing unwanted cellular proliferations.

Some embodiments are directed to methods of treating unwanted cellular proliferations (benign and malignant tumors, glandular (e.g., prostate hyperplasia) comprising administering to a subject in need thereof a therapeutically effective amount of at least one cobra toxin peptide composition.

Such peptide compositions can be administered alone or conjugated to a carrier or an antibody. For example, in certain embodiments, the peptide compositions can be administered intraperitoneally, intratumorally, intralesionally, intradermally, topically, transdermally, via an injection, implantation device, sustained release system etc., either alone or conjugated to a carrier. Alternatively, the peptide compositions can be expressed in vivo by administering a gene that expresses the peptides, by administering a vaccine that induces such production or by introducing cells, bacteria or viruses that express the peptide in vivo, because of genetic modification or otherwise.

In addition, the peptide compositions may be used in conjunction with other therapies for treating benign and malignant tumors and other unwanted or harmful cellular growths.

Both the foregoing general description and the following detailed description are exemplary and explanatory and are intended to provide further explanation of the embodiments as claimed. Other objects, advantages, and features will be readily apparent to those skilled in the art from the following detailed description of the embodiments.

In a broad aspect, there is provided herein a method of treating prostatic enlargement. In a particular aspect, the method is useful in the treatment of prostatic hyperplasia, especially benign prostatic hyperplasia. The present invention can also be used for the treatment of enlargement of the prostate with inflammation (prostatitis), and other such disorders.

In one aspect, there is provided herein a method for treating a subject in need thereof, comprising injecting a therapeutic amount of a therapeutic composition comprised of a cobra toxin or derivatives thereof into a prostate gland of the subject in an amount sufficient to diminish at least one symptom of a prostatic disorder.

In certain embodiments, the prostatic disorder comprises one or more of: prostatic hyperplasia, benign prostatic hyperplasia or prostatic enlargement.

In another aspect, there is provided herein a method for treating a prostatic disorder comprising injecting a therapeutic amount of a peptide composition comprised of a cobra toxin or derivative thereof into a prostate gland of a subject in need thereof sufficient to diminish at least one symptom of such disorder.

In certain embodiments, the cobra toxin peptide compositions comprise *naja naja atra* venom or a derivative thereof. In certain embodiments, the cobra toxin peptide compositions comprise a composition of matter comprising one or more of SEQ ID NOs:1-12.

The peptide compositions can be formulated in any pharmaceutically acceptable formulation in any pharmaceutically acceptable form. Such forms and formulations include liquids, powders, creams, emulsions, pills, troches, suppositories, suspensions, solutions, and the like.

The peptide compositions can also be used in any pharmaceutically acceptable form supplied by any manufacturer. Therapeutically effective amounts of the peptide compositions can be any amounts or doses that are less than a toxic dose, for example, less than about 3000 IU/70 kg male, preferably between 100 IU/70 kg male to 1200 IU/70 kg. The dosages can be given as a single dose, or as divided doses, for example, divided over the course of two or more weeks.

The peptide compositions may be administered by any suitable means. In certain embodiments, the peptide compositions may be administered by injection to an affected area. For example, the peptide compositions can be injected urethroscopically into the prostate with 200 IU with single or serial dosing.

A therapeutically effective amount of the peptide compositions is the dosage sufficient to induce at least temporary atrophy of the treated tissue. It is to be understood that dosing can be a single dosage or cumulative (serial dosing), and can be readily determined by one skilled in the art.

The peptide compositions may be delivered serially (i.e., one time per month, one time per every six months) so that the therapeutic effect can be optimized. Such a dosage schedule is readily determined by one skilled in the art based on, e.g., patient size and the condition to be treated, and will depend on many factors, including the cobra toxin selected, the condition to be treated, and other variables.

In a particular aspect, the present invention is directed to a method of treatment that is useful for the long-term control of the symptoms of prostatic enlargement, without the need for surgical intervention.

Therapeutic Applications

In general, the methods and compositions of the invention are useful for the treatment of any disease or condition associated with tissue hypertrophy and/or hyperplasia and other forms of unwanted tissue growth. In particular, the methods and compositions are useful for the treatment of BPH as described above. Compositions and methods of the invention may be tested in a variety of animal models. As described above, one aspect of the invention is a transgenic nonhuman animal model in which the effects of a composition on prostate cells can be tested, and differential effects on basal and luminal cells of the prostate can be evaluated. Alternative or additional animal models can be used. For example, rat, canine and primate (chimpanzee) animal models of BPH are known.

In other embodiments, other medically and/or cosmetically undesirable accumulations of adipose tissue can also be treated. In accordance with another embodiment of the present invention, an undesired accumulation of tissue is treated by local delivery of a composition comprising a therapeutic agent that inhibits growth of adipose cells or kills such cells. The composition may comprise a cell type specific therapeutic agent, e.g., a vector that directs expression of a therapeutic nucleic acid or polypeptide in a cell specific manner. The composition may comprise a tissue-selective delivery. Preferably, a composition comprising a tissue-selective or specific therapeutic agent, and optionally comprising a tissue-selective delivery vehicle is delivered locally, e.g., by injection or implantation, at a site of tissue whose reduction in size is desired.

Benign tumors, accumulations of fibrous tissue, scars, etc., can also be treated. Cysts, e.g., dermoid cysts, epidermal cysts, etc., that have a component of cell proliferation can also be treated by local administration of a composition of the invention comprising a cytotoxic or cytostatic therapeutic agent and, optionally, a tissue-selective delivery vehicle.

Pharmaceutical Compositions and Additional Delivery Methods

Suitable preparations, e.g., substantially pure preparations of therapeutic agents that inhibit cell survival or proliferation, optionally together with a delivery vehicle may be combined with pharmaceutically acceptable carriers, diluents, solvents, etc., to produce a pharmaceutical composition. Any of the compositions described herein may be formulated as a pharmaceutical composition suitable for administration to patients.

In certain embodiments, the pharmaceutical composition detectably reduces tissue volume or inhibits continued growth of the tissue. Administration of the composition measurably reduces tissue volume relative to the volume that would exist in the absence of the composition. It is to be understood that the pharmaceutical compositions, when administered to a subject, are preferably administered for a time and in an amount sufficient to treat or prevent the disease or condition for whose treatment or prevention they are administered.

Also provided are pharmaceutically acceptable compositions comprising a pharmaceutically acceptable derivative (e.g., a prodrug) of any of the therapeutic agents of the invention, by which is meant any non-toxic salt, ester, salt of an ester or other derivative of a compound that, upon administration to a recipient, is capable of providing, either directly or indirectly, the effect of a therapeutic agent of the invention.

In certain preferred embodiments, therapeutic compositions are delivered locally to hypertrophic tissues. However, in other embodiments, the therapeutic compositions may be formulated for delivery by any available route.

The term "pharmaceutically acceptable carrier, adjuvant, or vehicle" refers to a non-toxic carrier, adjuvant, or vehicle that does not destroy the pharmacological activity of the compound with which it is formulated. Non-limiting examples of suitable pharmaceutically acceptable carriers, adjuvants or vehicles that may be used in the compositions of this invention include: ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Solvents, dispersion media, coatings, antibacterial and antifungal agents, isotonic and absorption delaying agents, and the like, compatible with pharmaceutical administration may be included. Supplementary active compounds, e.g., compounds independently active against the disease or clinical condition to be treated, or compounds that enhance activity of an inventive compound, can also be incorporated into the compositions.

Pharmaceutically acceptable salts include those derived from pharmaceutically acceptable inorganic and organic acids and bases. Non-limiting examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and N+(C1-4 alkyl)4 salts. Also, water or oil-soluble or dispersible products may be also used.

A pharmaceutical composition is formulated to be compatible with its intended route of administration. Solutions or suspensions used for parenteral (e.g., intravenous), intramuscular, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use typically include sterile aqueous solutions (where water soluble) or dispersions and sterile powders for the extemporaneous preparation of sterile injectable solutions or dispersion. The pharmaceutical composition should be sterile, if possible, and should be fluid to the extent that easy syringability exists if it is to be delivered by means that use a syringe.

Sterile injectable solutions can be prepared by incorporating the active agent in the required amount in an appropriate solvent with one or a combination of ingredients enumerated above, as required, followed by filtered sterilization. Preferably solutions for injection are free of endotoxin. Generally, dispersions are prepared by incorporating the active agent into a sterile vehicle which contains a basic dispersion medium and the required other ingredients from those enumerated above. In the case of sterile powders for the preparation of sterile injectable solutions, the preferred methods of preparation are vacuum drying and freeze-drying which yield a powder of the active ingredient plus any additional desired ingredient from a previously sterile-filtered solution thereof. Preferred pharmaceutical formulations are stable under the conditions of manufacture and storage and may be preserved against the contaminating action of microorganisms. In general, the relevant carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, or sodium chloride in the composition. Prolonged absorption of injectable compositions can be brought about by including in the composition an agent which delays absorption, for example, aluminum monostearate and gelatin.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

In addition to the delivery vehicles described above, in certain embodiments of the invention, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polyethers, and polylactic acid.

Another method of administering a cobra toxin peptide is by a transdermal or transcutaneous route.

Another method of administering a cobra toxin peptide is in conjunction with a surgical or similar procedure employed to physically excise, ablate or otherwise kill or destroy tumor or other tissue or cellular elements required or desired to be removed or destroyed wherein the peptide is administered to the immediate area(s) surrounding the area(s) where the tumor or other tissue was removed in order to destroy or impede the growth of any tumor cells or other cellular elements not removed or destroyed by the procedure.

Another method of administering a cobra toxin peptide is by implantation of a device within the tumor or other tissue to be treated. One example of such an embodiment is the implantation of a wafer containing the cobra toxin peptide in the tumor or other tissue to be treated. The wafer releases a therapeutic dose of peptide into the tissue over time. Alternatively or additionally, the cobra toxin peptide may be administered locally via implantation into the affected area of a membrane, sponge, or other appropriate material onto which the cobra toxin peptide has been absorbed. Where an implantation device is used, the device may be implanted into any suitable tissue or organ, and delivery of the cobra toxin peptide may be directly through the device via bolus, or via continuous administration, or via catheter using continuous infusion.

Methods for preparation of such formulations will be apparent to those skilled in the art. Liposomal suspensions can also be used as pharmaceutically acceptable carriers. These can be prepared according to methods known to those skilled in the art. It is typically advantageous to have compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit high therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

A therapeutically effective amount of a pharmaceutical composition typically ranges from about 0.001 to 100 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The pharmaceutical composition can be administered at various intervals and over different periods of time as required, e.g., multiple times per day, daily, every other day, once a week for between about 1 to 10 weeks, between 2 to 8 weeks, between about 3 to 7 weeks, about 4, 5, or 6 weeks, etc. The skilled artisan will appreciate that certain factors can influence the dosage and timing required to effectively treat a subject, including but not limited to the severity of the disease or disorder, previous treatments, the general health and/or age of the subject, and other diseases present. Generally, treatment of a subject with an inventive composition can include a single treatment or, in many cases, can include a series of treatments.

Exemplary doses include milligram or microgram amounts of the inventive compounds per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram.) In some embodiments of the invention doses much smaller than these may be used. It is furthermore understood that appropriate doses depend upon the potency of the agent, and may optionally be tailored to the particular recipient, for example, through administration of increasing doses until a preselected desired response is achieved. It is understood that the specific dose level for any particular subject may depend upon a variety of factors including the activity of the specific compound employed, the age, body weight, general health, gender, and diet of the subject, the time of administration, the route of administration, the rate of excretion, any drug combination, the amount of tissue to be reduced, and the amount of reduction desired.

The present invention includes the use of inventive compositions for treatment of nonhuman animals including, but not limited to, companion animals such as dogs and cats, agriculturally important animals such as ruminants (e.g., cows), sheep, horses, etc. Accordingly, doses and methods of administration may be selected in accordance with known principles of veterinary pharmacology and medicine.

The invention further provides pharmaceutical compositions comprising two or more therapeutic agents of the invention, e.g., two or more nucleic acid constructs such as those described above. The invention further provides a pharmaceutical composition comprising a therapeutic agent of the invention and a second agent, e.g., a hormone, anti-thyroid drug, etc.

EQUIVALENTS AND SCOPE

Those skilled in the art will recognize, or be able to ascertain using no more than routine experimentation, many equivalents to the specific embodiments of the invention described herein. The scope of the present invention is not intended to be limited to the above Description, but rather is as set forth in the appended claims. In the claims articles such as "a,", "an" and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context.

The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim. In particular, any claim that is dependent on another claim can be modified to include one or more limitations found in any other claim that is dependent on the same base claim. Furthermore, where the claims recite a composition, it is to be understood that methods of administering the composition according to any of the methods disclosed herein, and methods of using the composition for any of the purposes disclosed herein are included, and methods of making the composition according to any of the methods of making disclosed herein are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc.

The inclusion of a "providing" step in certain methods of the invention is intended to indicate that the composition or device is administered to treat a disease or condition characterized by inappropriate or excessive noncancerous tissue growth, e.g., BPH. Thus the subject will have or be at risk of a disease or condition characterized by inappropriate or excessive noncancerous tissue growth, and the composition or device is administered to treat the disorder, typically upon the sound recommendation of a medical or surgical practitioner, e.g., a urologist in the case of BPH, who may or may not be the same individual who administers the composition or device.

The invention includes embodiments in which a step of providing is not explicitly included and embodiments in which a step of providing is included. The invention also includes embodiments in which a step of identifying the subject as being at risk of or suffering from a disease or condition characterized by inappropriate or excessive noncancerous tissue growth, e.g., BPH, is included.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any polypeptide or polynucleotide), any method of administration, any disorder or condition or characteristic(s) thereof, or any subject characteristic(s) can be excluded from any one or more claims, for any reason, whether or not related to the existence of prior art.

Moreover, the embodiments include other proteins that contain, in whole or part, a cobra toxin peptide, whereby the proteins preferably possess the same, similar, or enhanced bioactivity as the cobra toxin peptide. Using the guidelines provided herein, a person ordinarily skilled in the art could synthesize specific proteins based on the amino acid sequence for a cobra toxin peptide found to be an effective agent for causing cell death and test them for efficacy as agents for causing the desired effects.

The embodiments also encompass peptides comprising two or more peptides joined together. To the extent that a cobra toxin peptide has the desired biological activity, it follows that two such peptides would also possess the desired biological activity.

Peptides and fragments, variants, derivatives, homologues, fusion proteins and mimetics thereof encompassed by this embodiment can be prepared using methods known to those of skill in the art, such as recombinant DNA technology, protein synthesis and isolation of naturally occurring peptides, proteins, AD7c-protein and fragments, variants, derivatives and homologues thereof.

Peptides and fragments, variants, derivatives, homologues, fusion proteins and mimetics thereof can be prepared from other peptides, proteins, and fragments, variants, derivatives and homologues thereof using methods known to those having skill in the art. Such methods include (but are not limited to) the use of proteases to cleave the peptide, or protein into the desired peptides.

Peptides and fragments, homologs, variants, fusion proteins, peptide mimetics, derivatives and salts thereof also can be made using conventional peptide synthesis techniques known to the skilled artisan. Advantages exist for using a mimetic of a given peptide rather than the peptide itself. In general, peptide mimetics are more bioavailable, have a longer duration of action and can be cheaper to produce than the native proteins and peptides.

Thus, the peptides described above have utility in the development of such small chemical compounds with similar biological activities and therefore with similar therapeutic utilities. Peptide mimetics can be developed using combinatorial chemistry techniques and other techniques known in the art.

The present invention satisfies a need in the art for treatments that can remove benign tumors with less risk and fewer of the undesirable side effects of surgery. A method for removing benign tumors in surgically hazardous areas such as in deep locations in the body (e.g., brain, heart, lungs, and others) is particularly needed.

The method of treating conditions where cells must be removed can be used in conjunction with conventional methods of treating such conditions, such as surgical excision, chemotherapy, and radiation. The peptides can be administered before, during, or after such conventional treatments.

The condition to be treated can also be a hyperplasia, hypertrophy, or overgrowth of a tissue from, for example, lung, breast, stomach, pancreas, prostate, bladder, bone, ovary, skin, kidney, sinus, colon, intestine, stomach, rectum, esophagus, brain and its coverings, spinal cord and its coverings, muscle, connective tissue, adrenal, parathyroid, thyroid, uterus, testis, pituitary, reproductive organs, liver, gall bladder, eye, ear, nose, throat, tonsils, mouth, and lymph nodes and lymphoid system.

Other conditions that can be treated using the method of the embodiments are virally, bacterially, or parasitically altered tissue. Still other conditions to be treated can also be a malformation or disorder of a tissue and/or a cosmetic modification to a tissue.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. All publications, including patents and non-patent literature, referred to in this specification are expressly incorporated by reference herein.

Intraprostatic Injection of Cobra Venom as a Therapy for BPH.

Cobra venom consists of a multitude of individual toxins, such as various neurotoxins and cardiotoxins. Cardiotoxins (Ctx), a group of major polypeptides of around 60 amino acid residues, present abundantly in the elapid family of snakes. The inventors herein evaluated the use of Cardiotoxin-D as an alternative to traditional treatments for BPH resulting in less morbidity.

Materials and Methods

The cobra toxin used was from the subspecies *Naja naja atra* (Taiwanese Cobra). Source: Miami Serpentarium (Salt Lake City, Utah)

Fraction Separation.

Ion-exchange chromatography using BioRex 70 followed by second ion-exchange using a concave ammonium acetate gradient from 0.5 to 2.0 M, followed by dialysis of individually collected peak fractions (cardiotoxins B, C, and D) and lyophilization.

Component Fraction Used.

Cardiotoxin D (CTx-D), the letter "D" specifies that this CTX is the most basic of the 4 CTX that are purified in the second step of ion-exchange chromatography and so eluted last from the column. Molecular Weight: 6827.4 grams. LD50 Rat-2 mg/kg (i.v.).

For a possible negative control the inventors also have acylated CTX-D from NNS. Acylation selectively modifies the 3 tyrosines in the CTX and renders it cytotoxically inactive. L1AD3 is a synthetic homologue of Loop 1 of NNA CTX-D that has a much lower potency than that of whole CTx-D itself. The advantage of L1AD3 is that it has no heart toxicity.

Animals.

Eighteen adult male Sprague-Dawley rats (420-560 g) were used in this study. The animals were housed in the animal care center under controlled lighting conditions (lights on 6 AM-6 PM), with food and water always available. The animals were monitored for behavior, food and water intake, and weight. Subsequent experiments were approved by the University of Toledo's Institutional Animal Care and Use Committee.

The rats were divided into 3 groups of six rats each. Using a single injection of 0.1 mL into both the right and left ventral lobes of the prostate, each rat received an intraprostatic injection of either saline, cardiotoxin, or Botox A (Table 1).

Table 1:

TABLE 1

| | Injections | |
|---|---|---|
| | Concentration | Dose |
| Saline, n = 6 | 0.9% NS | 0.2 mL |
| Botox A, n = 6 | 5 U | 0.2 mL |
| CTx, n = 6 | 3 mg/mL | 0.2 mL |

Toxins.

Botulinum toxin type A (Botox, Allergen) is available in vials containing 100 U of lyophilized toxin, which is stored at −20 degrees C. until use. The toxin was reconstituted with 4 mL 0.9% saline (1 mL=25 U) without preservatives and used within 4 hours.

Lyophilized venom was obtained from the Miami Serpentarium (Salt Lake City, Utah). The cardiotoxin fraction of *N. naja atra* venom was obtained by ion-exchange chromatography using BioRex 70. Individual components of that fraction, cardiotoxins B, C, and D (CTx is an abbreviation subsequently used for cardiotoxin-D), were obtained by a second ion-exchange step, using a concave ammonium acetate gradient from 0.5 to 2.0 M, followed by dialysis of individually collected peak fractions and lyophilization. Prior to use, cardiotoxins were dissolved in distilled, sterile water to 1 mg/mL, from which concentration an aliquot was diluted using RPMI 1640 or complete medium. Usually, 50 microliters diluted toxin at twice the final concentration was added to 50 microliter cell suspension in the wells of microtiter plates.

Injections.

Rats were anesthetized with isoflurane gas. The hair was shaved and the incision region was scrubbed with Betadine. A lower abdominal midline incision was made providing exposure to the bladder and prostate. 0.1 mL of toxin or saline was injected into each right and left ventral lobe using a 30-gauge needle. The abdominal wall and skin were then closed in two layers. After 2 weeks the animals were sacrificed by an overdose of sodium Pentobarbital (200 mg/kg i.p.) The prostates were removed en bloc along with the bladder and urethra. The prostates were then carefully dissected from the bladder neck and urethra, weighed and fixed in 10% phosphate buffered formalin.

Histology.

The fixed prostates were embedded in paraffin and sectioned at a thickness of 4 microns. Sections were stained with hematoxylin and eosin and analyzed for morphology. Immunohistochemical analysis was performed on prostate sections for evidence of apoptosis with TUNEL stain (terminal deoxynucleotidyl-mediated deoxyuridine triphosphate nick end labeling) using a commercially available kit (GenScript Corporation, Piscataway, N.J.), and for cellular proliferation with PCNA stain (proliferating cell nuclear antigen) using a commercially available kit (Invitrogen Corporation, Camarillo, Calif.). A stained slide from each animal was randomly assigned a number in a blind fashion. Under 400× magnification, four random areas of the ventral prostate from each animal were examined and the total numbers of stained and unstained cells were counted in the entire field. This was done for both TUNEL and PCNA stained slides for each animal. The mean number of stained and unstained cells was determined for each animal.

Statistics. Comparison of continuous variables between groups of rats was performed using one-way analysis of variance (ANOVA) with the Turkey post hoc test to compare individual pairings of groups. $p<0.05$ represents statistical significance.

Results

Prostate Volume.

The inventors observed a significant decrease in prostate size of rats injected with CTx when compared to the prostates of rats injected with BTA or saline (see Table 2 and Table 7).

Table 2: Prostate Weight

TABLE 2

Prostate Weight.

| Group | Prostate Wt (grams) | | | Prostate Wt /100 g Body Wt | | |
|---|---|---|---|---|---|---|
| | Mean | SD | SEM | Mean | SD | SEM |
| Saline | 2.634 | 0.265 | 0.119 | 0.531 | 0.071 | 0.032 |
| BTA | 2.627 | 0.326 | 0.146 | 0.586 | 0.064 | 0.029 |
| CTx | 1.785 | 0.140 | 0.063 | 0.362 | 0.112 | 0.080 |

Histology.

Figure 2:
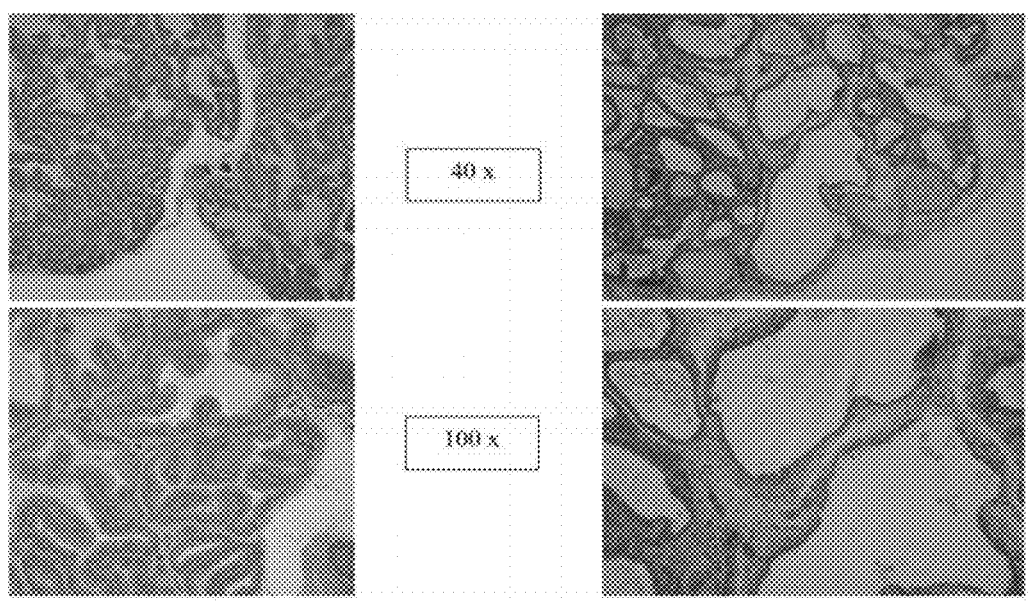

Two weeks post intraprostatic injection, BTA and CTx induced prostatic atrophy of the glandular component with flattening of the epithelial lining. FIG. 1 and FIG. 2 contain gross photos and histology photographs of one of the rat prostates injected with cobra toxin showing atrophy of the injected prostatic lobe.

TUNEL staining revealed a significant increase in the number of apoptotic cells in both the BTA and CTx injected prostates as compared to the saline injected prostates. There was no significant difference in the number of apoptotic cells between the CTx and BTA groups (see Table 3 and Table 7).

PCNA staining demonstrated a significant increase in cellular proliferation two weeks following BTA injection when compared to the saline and CTx injected groups (see Table 4 and Table 7).

Table 3: TUNEL Assay.

TABLE 3

TUNEL Assay.

| | # of Apoptotic Cells | | |
|---|---|---|---|
| Group | Mean | SD | SEM |
| Saline | 38.8 | 42.1 | 18.8 |
| BTA | 211.1 | 111.3 | 49.8 |
| CTx | 246.4 | 42.9 | 19.2 |

Table 4: PCNA Assay.

TABLE 4

PCNA Assay

| | # of Proliferating Cells | | |
|---|---|---|---|
| Group | Mean | SD | SEM |
| Saline | 0.6 | 0.8 | 0.3 |
| BTA | 26.2 | 23.6 | 10.6 |
| CTx | 17.1 | 6.9 | 3.5 |

Body Weight.

There was a significant loss in body weight in rats 2 weeks post intraprostatic injection with BTA. The body weights of the animals injected with CTx or saline were slightly higher at sacrifice than prior to intraprostatic injection (see Table 5 and Table 6). No other significant complications (i.e., urinary retention, or limb weakness) were noted in any group.

Table 5: Body Weight.

TABLE 5

Body Weight

| | Pre-Injection Wt (grams) | | 2 wks Post-Injection Wt (grams) | |
|---|---|---|---|---|
| Group | Mean | SD | Mean | SD |
| Saline | 485 | 36 | 499 | 53 |
| BTA | 501 | 40 | 449 | 37 |
| CTx | 485 | 36 | 494 | 23 |

Table 6: Change in Body Weight

TABLE 6

Change in Body Weight

| Group | Mean | SD | SEM |
|---|---|---|---|
| Saline | 8.000 | 19.380 | 8.667 |
| BTA | −51.667 | 4.844 | 2.166 |
| CTx | 8.667 | 17.096 | 7.646 |

Table 7: Comparison Among Groups with Statistical Significance.

TABLE 7

Comparison Among Groups with Statistical Significance

| Groups | Change in Body Wt. | Prostate Wt. | Prostate Wt./ 100 g Body Wt. | TUNEL Assay | PCNA Assay |
|---|---|---|---|---|---|
| Saline vs. BTA | p < 0.05 | p = 0.999 | p = 0.261 | p < 0.003 | p < 0.022 |
| Saline vs. CTx | p = 0.997 | p < 0.000 | p < 0.04 | p < 0.001 | p = 0.184 |
| BTA vs. CTx | p < 0.5 | p < 0.000 | p < 0.04 | p = 0.686 | p = 0.571 |

Results.

A decrease in size of the injected prostatic lobe was found in all rats. Prostatic atrophy in the glandular component with flattening of the epithelial lining was seen histologically in rats receiving either toxin. No significant complications (i.e. weight loss, urinary retention, or limb weakness) were noted.

These results provide evidence of therapeutic applications for CTX in comparison to botulinim toxin A (BTA) as a treatment for BPH. The inventors herein found a statistically significant decrease in prostate weight in the rats treated with CTX when compared with the rats treated with both saline and BTA. Furthermore, this decrease in prostate weight was not seen in the rats treated with BTA compared to those treated with saline. Importantly, this result is not consistent with the previous work by Doggweiler et al. Botox-induced prostatic involution, *The Prostate*, 1998; 37:44-50, which showed that intraprostatic injection of 5 units of BTA led to a decrease in prostatic weight one week after injections. In comparison, the inventors herein did not show a statistically significant decrease in prostatic weight following injection of 5 units of BTA two weeks after injections, despite demonstrating histological atrophy of the glandular component with flattening of the epithelial lining. While not wishing to be bound by theory, the inventors herein now believe that the difference in study outcomes may be the result of cellular regeneration of glandular cells at two weeks following intraprostatic injection of BTA. This theory is supported by the significant increase in the number of proliferating cells seen in the BTA group compared with the saline group on PCNA staining.

In addition, the present results demonstrate a statistically significant decrease in body weight in those rats treated with single BTA injections when compared to rats treated with both saline and CTX. This finding, again, contrasts previous findings; i.e., Doggweiler et al. noted body weight loss only in those rats that underwent serial injections.

The results herein show that injections of both BTA and CTX led to diffuse prostatic atrophy in the glandular component with flattening of the epithelial lining. Both BTA and CTX injected rat prostates showed diffuse cellular apoptosis (TUNEL assay) two weeks following injections. The increased number of apoptotic cells following BTA and CTX injections was statistically significant when compared with the prostates treated with saline. However, when comparing BTA and CTX treated prostates, the results were not statistically significant.

These results also show that CTX offers a similar histological effect on the rat prostate to that of BTA, and may, by extension, offer similar efficacy in humans.

Further, while not wishing to be bound by theory, the inventors herein now believe that another advantage of CTX is that CTX can have antinociceptive properties, and that the analgesic properties of cobra cardiotoxins may be also be of therapeutic value in the setting of intraprostatic injections by serving to minimize the pain of treatment.

In Vitro Data of Cardiotoxins from Various *Naja* Species (*Naja-naja atra*, NNN-*Naja naja naja*; NNS-*Naja naja siamensis*)

Figure 3A:
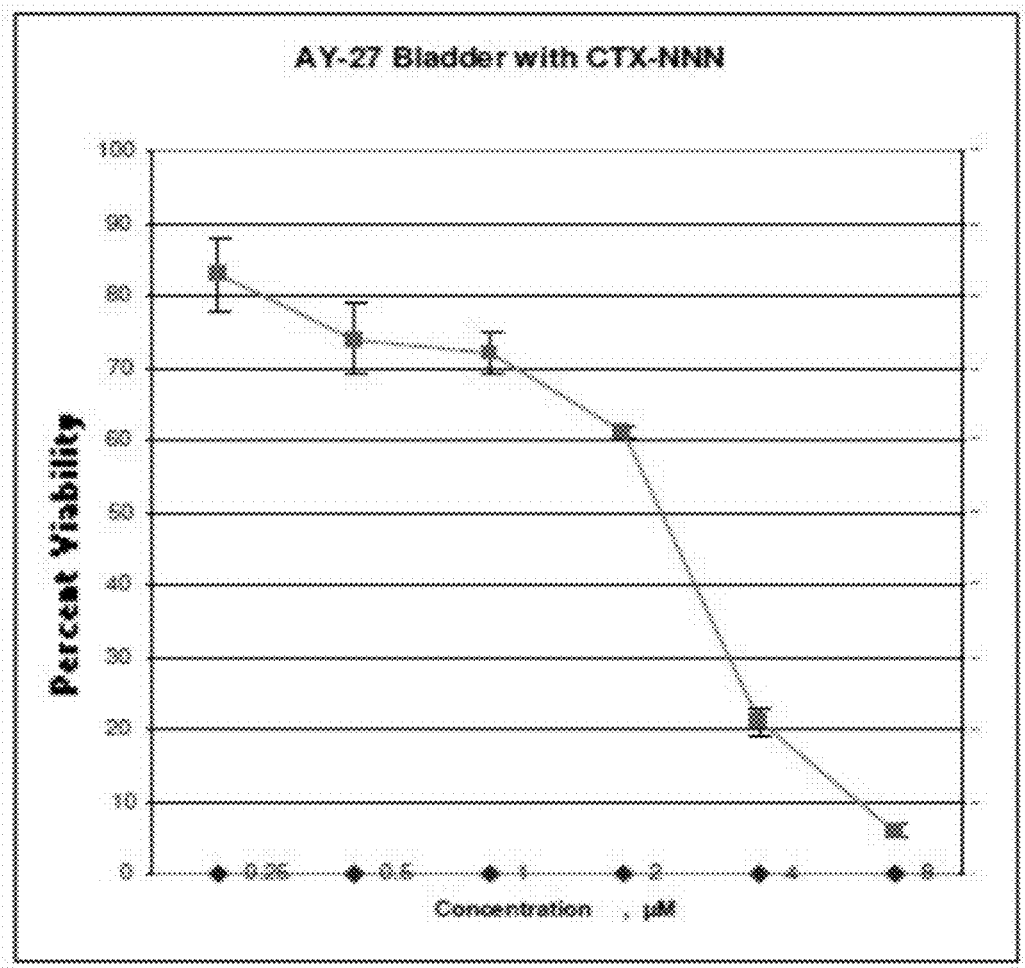
FIG. 3a is a graph for AY-27 bladder with CTX-Atra, showing the percent viability for various concentrations.

FIG. 3a is a graph for AY-27 bladder with CTX-NNN, showing the percent viability for various concentrations.

Figure 3B:
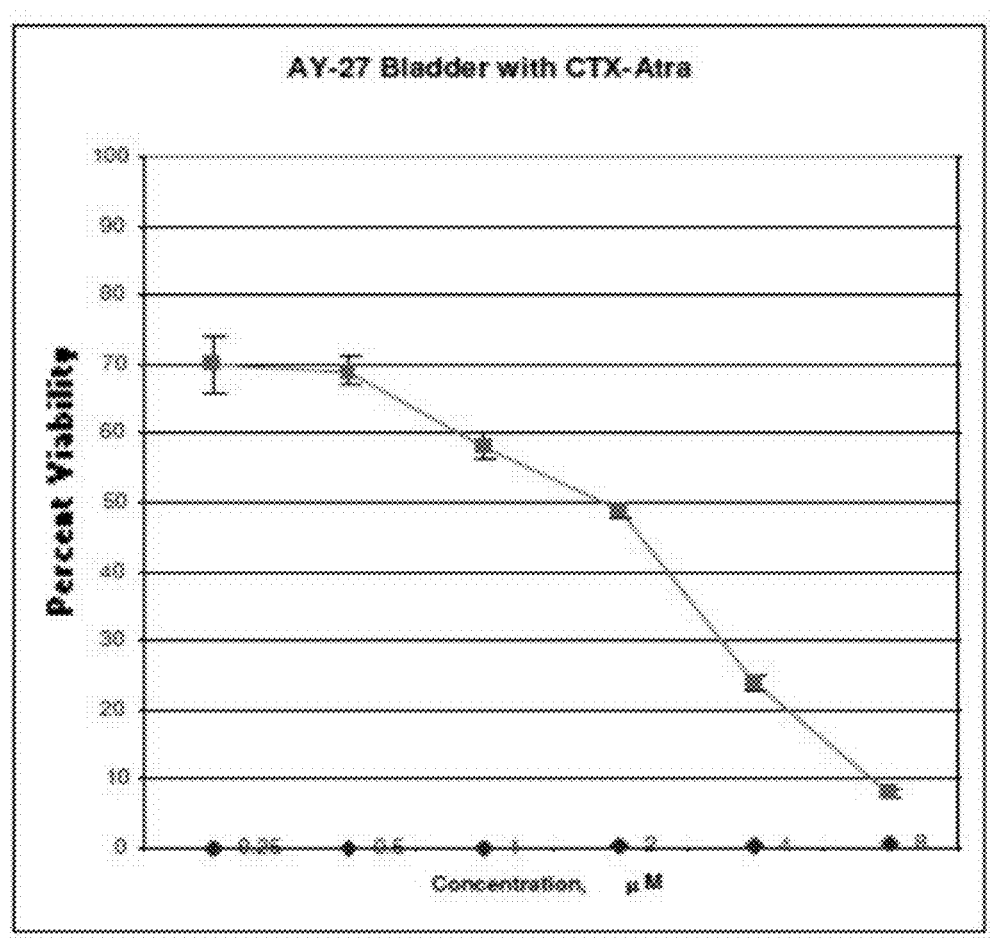
FIG. 3b is a graph for AY-27 bladder with CTX-NNN, showing the percent viability for various concentrations.

FIG. 3b is a graph for AY-27 bladder with CTX-Atra, showing the percent viability for various concentrations.

Figure 4A:
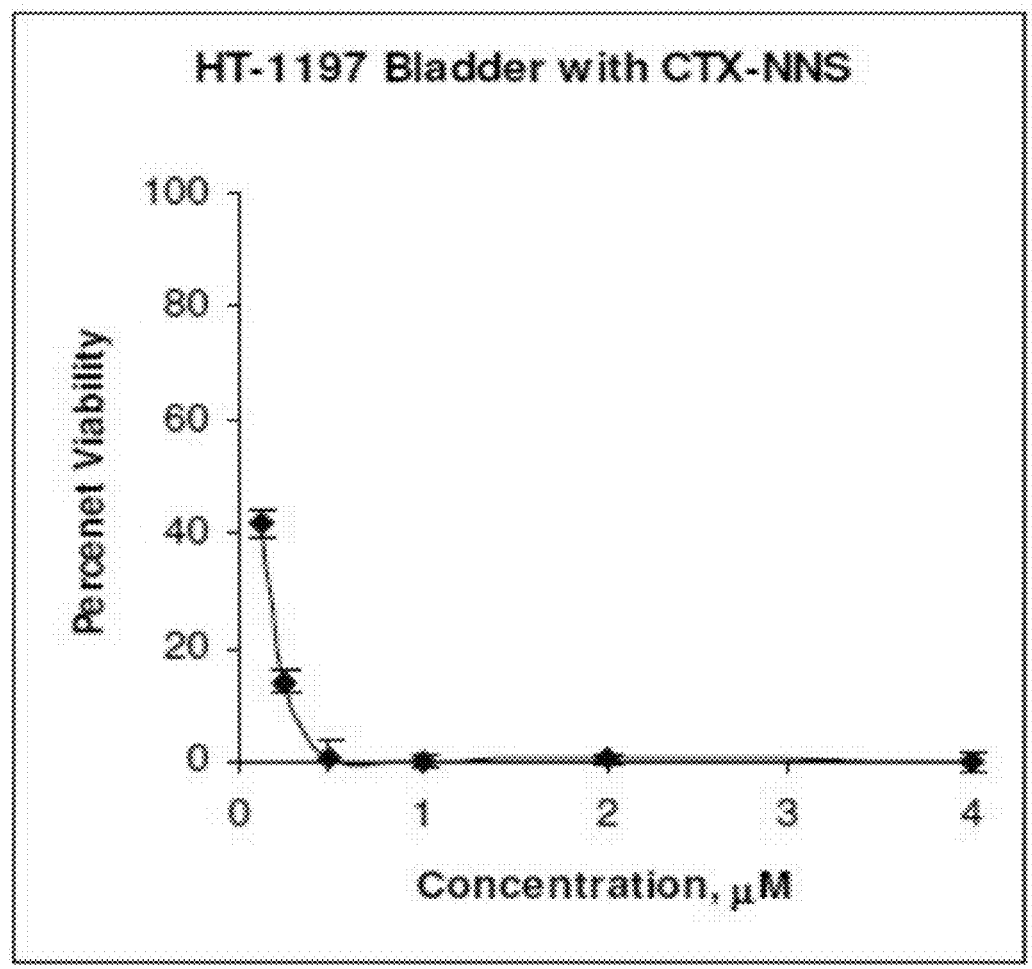
FIG. 4a is a graph for HT-1197 bladder with CTX-NNS, showing the percent viability for various concentrations.

FIG. 4a is a graph for HT-1197 bladder with CTX-NNS, showing the percent viability for various concentrations.

Figure 4B:
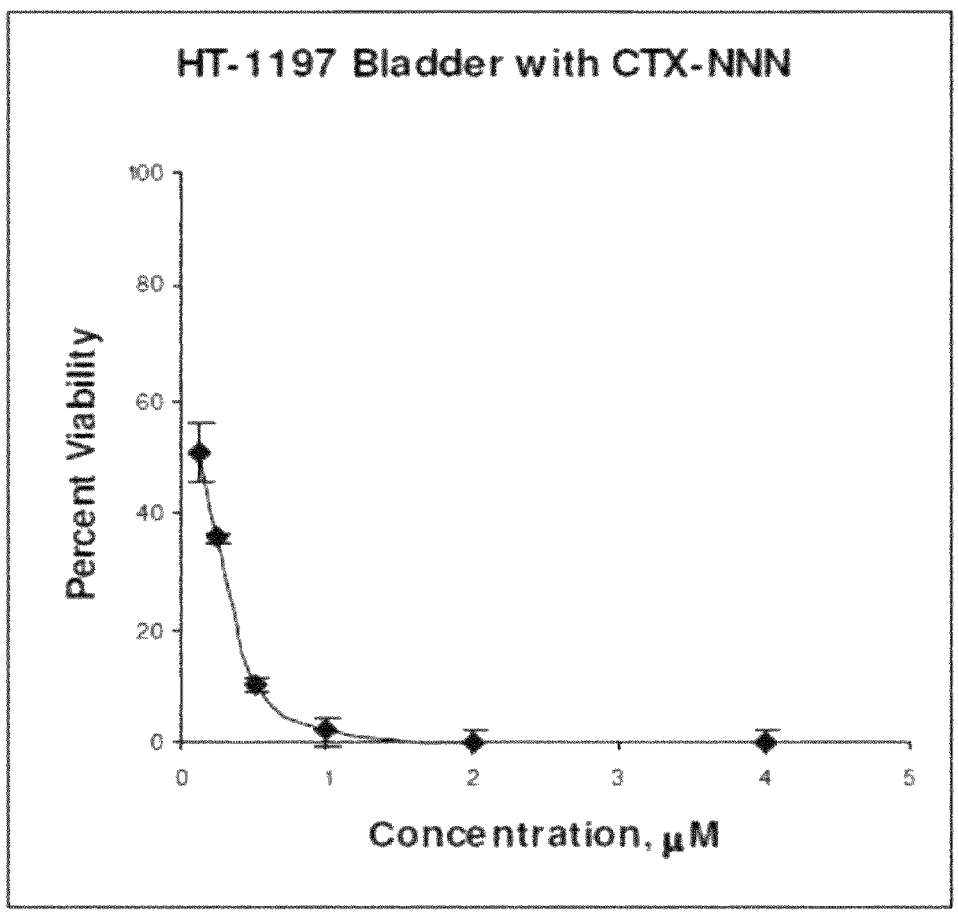
FIG. 4b is a graph for HT-1197 bladder with CTX-NNN, showing the percent viability for various concentrations.

FIG. 4b is a graph for HT-1197 bladder with CTX-NNN, showing the percent viability for various concentrations.

Figure 5A:
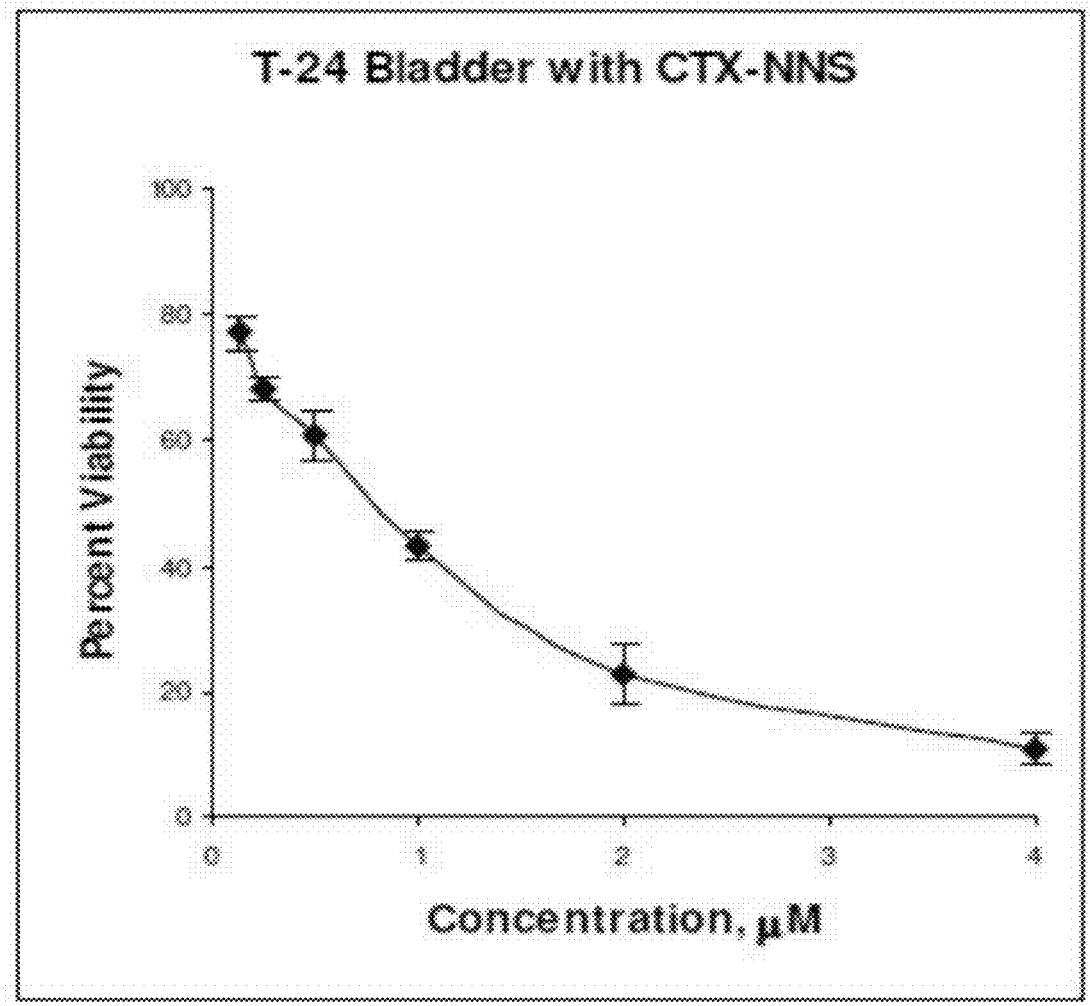
FIG. 5a is a graph for T-24 bladder with CTX-NNS, showing the percent viability for various concentrations.

FIG. 5a is a graph for T-24 bladder with CTX-NNS, showing the percent viability for various concentrations.

Figure 5B:
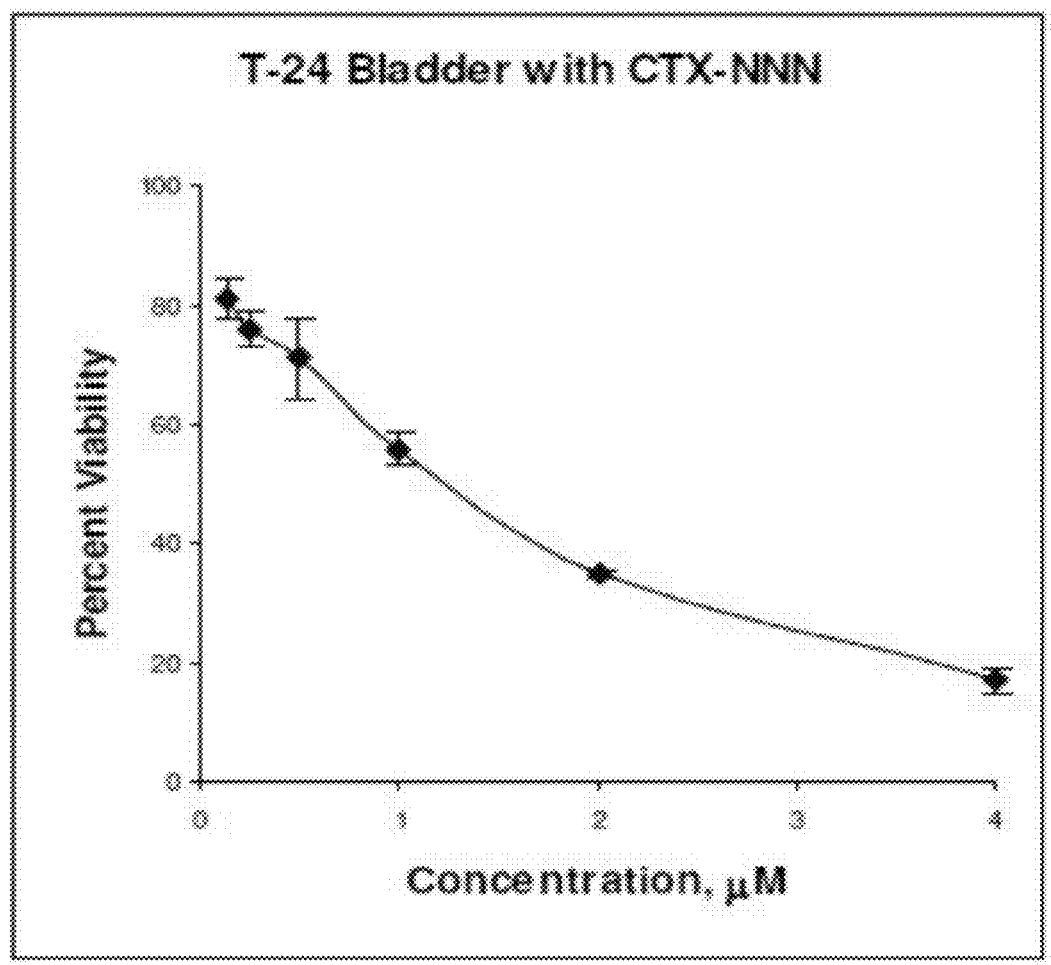
FIG. 5b is a graph for T-24 bladder with CTX-NNN, showing the percent viability for various concentrations.

FIG. 5b is a graph for T-24 bladder with CTX-NNN, showing the percent viability for various concentrations.

Figure 6A:
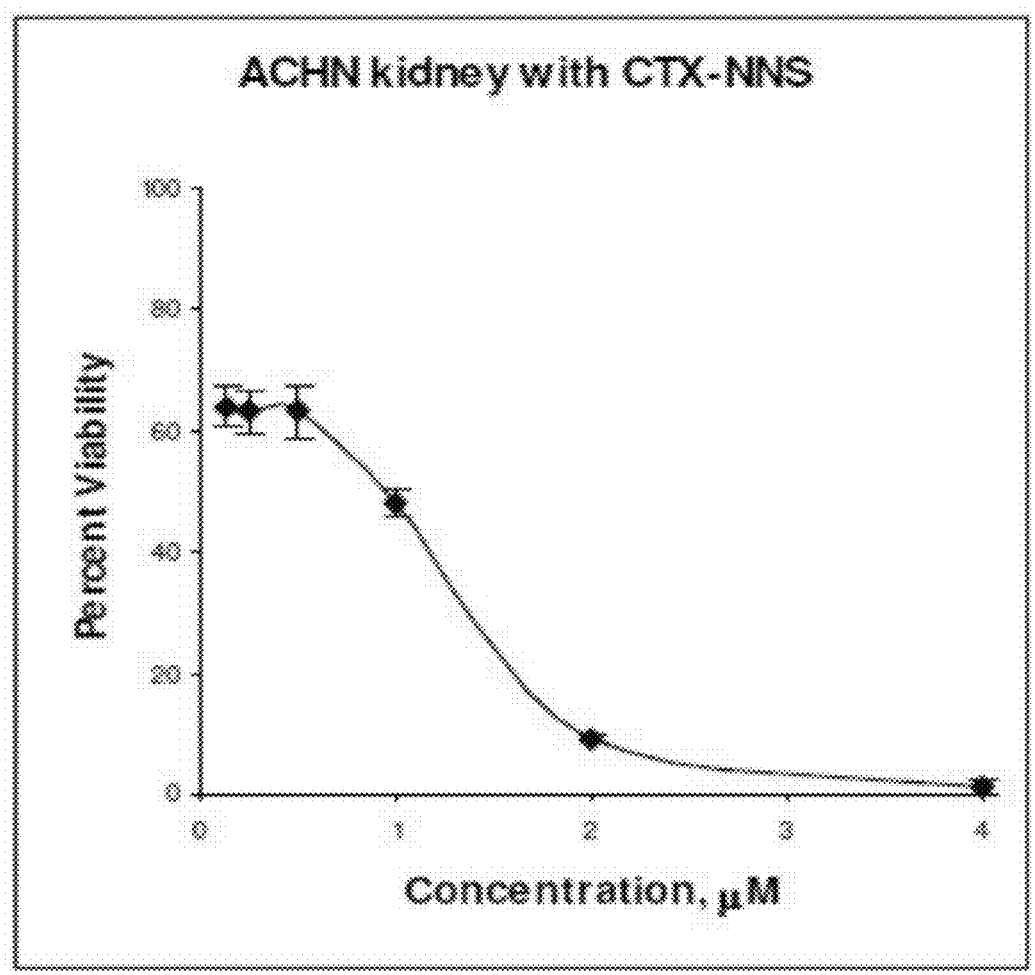
FIG. 6a is a graph for ACHN kidney with CTX-NNS, showing the percent viability for various concentrations.

FIG. 6a is a graph for ACHN kidney with CTX-NNS, showing the percent viability for various concentrations.

Figure 6B:
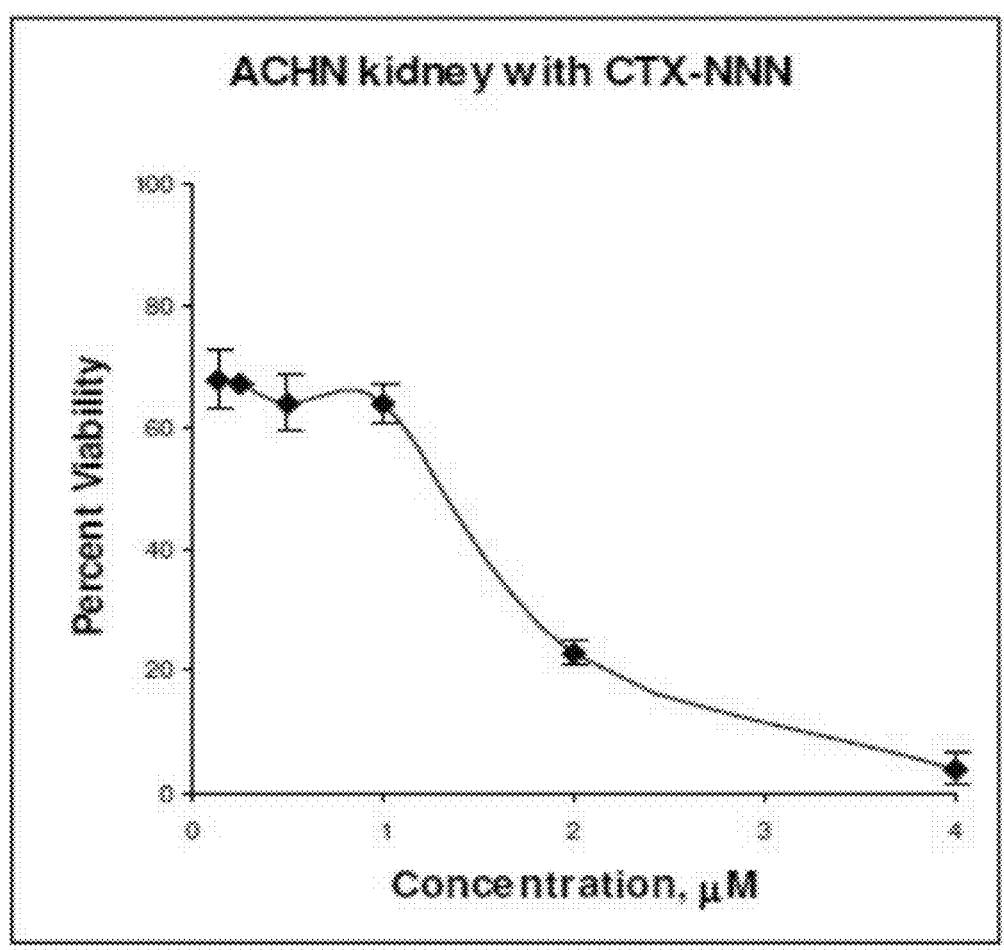
FIG. 6b is a graph for ACHN kidney with CTX-NNN, showing the percent viability for various concentrations.

FIG. 6b is a graph for ACHN kidney with CTX-NNN, showing the percent viability for various concentrations.

Figure 7A:
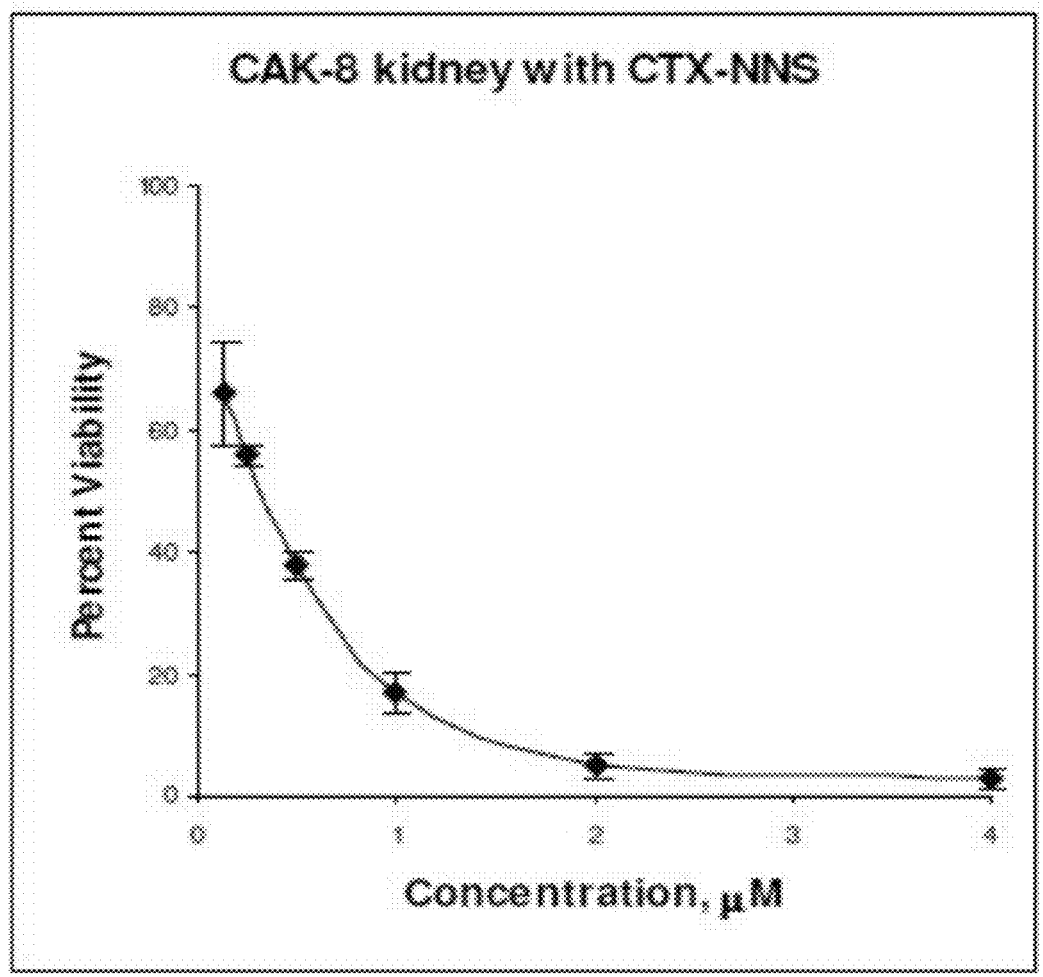
FIG. 7a is a graph for CAK-8 kidney with CTX-NNS, showing the percent viability for various concentrations.

FIG. 7a is a graph for CAK-8 kidney with CTX-NNS, showing the percent viability for various concentrations.

Figure 7B:
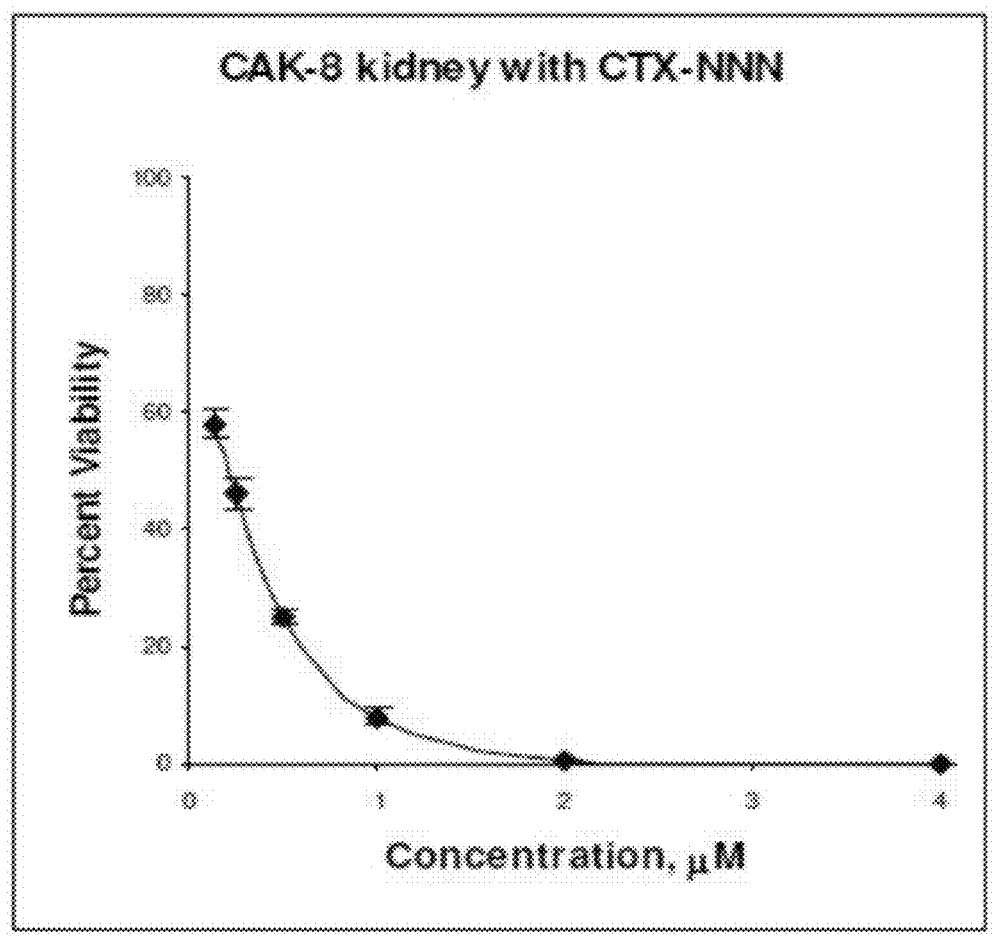
FIG. 7b is a graph for CAK-8 kidney with CTX-NNN, showing the percent viability for various concentrations.

FIG. 7b is a graph for CAK-8 kidney with CTX-NNN, showing the percent viability for various concentrations.

Figure 8A:
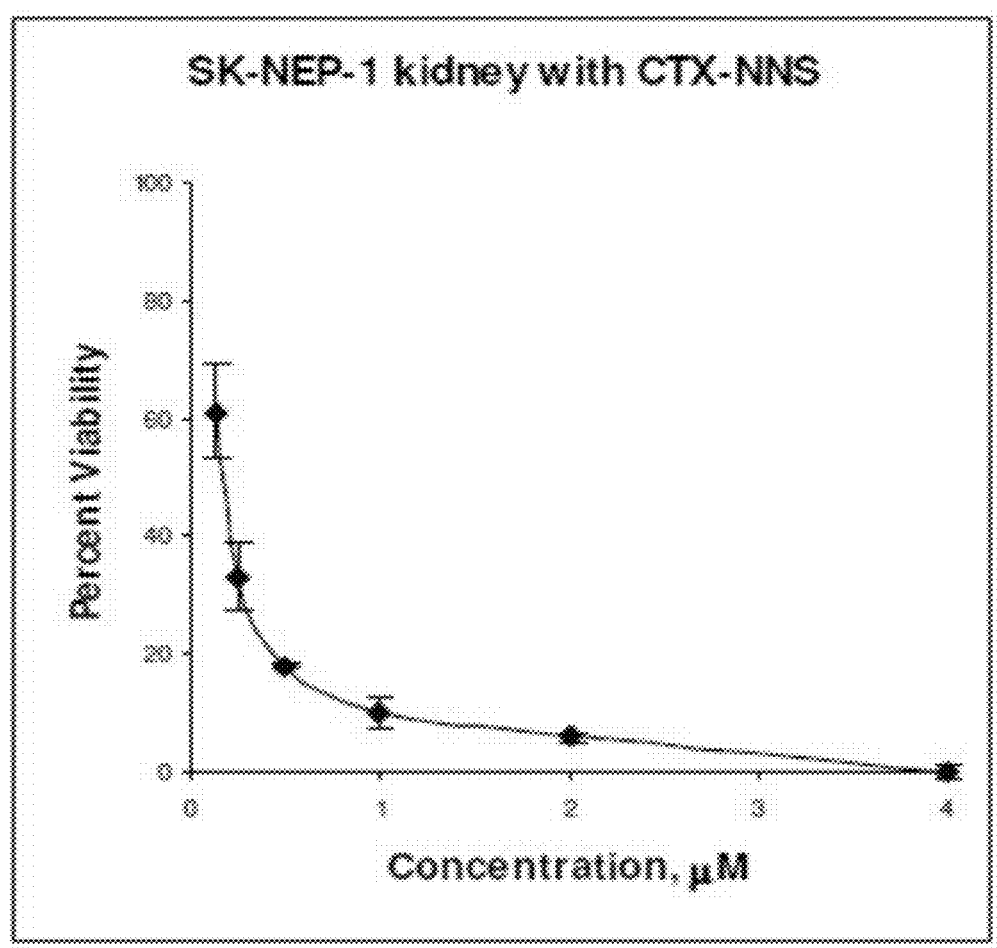
FIG. 8a is a graph for SK-NEP-1 kidney with CTX-NNS, showing the percent viability for various concentrations.

FIG. 8a is a graph for SK-NEP-1 kidney with CTX-NNS, showing the percent viability for various concentrations.

Figure 8B:
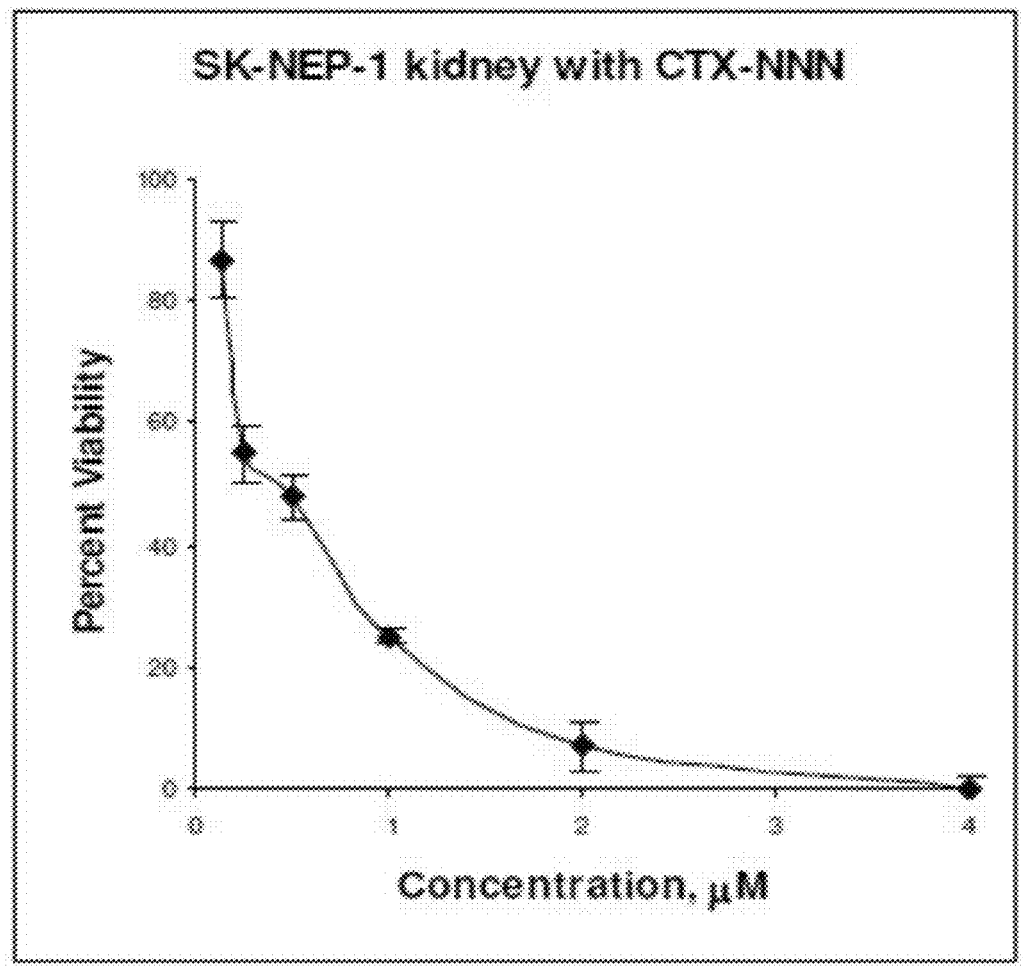
FIG. 8b is a graph for SK-NEP-1 kidney with CTX-NNN, showing the percent viability for various concentrations.

FIG. 8b is a graph for SK-NEP-1 kidney with CTX-NNN, showing the percent viability for various concentrations.

Figure 9A:
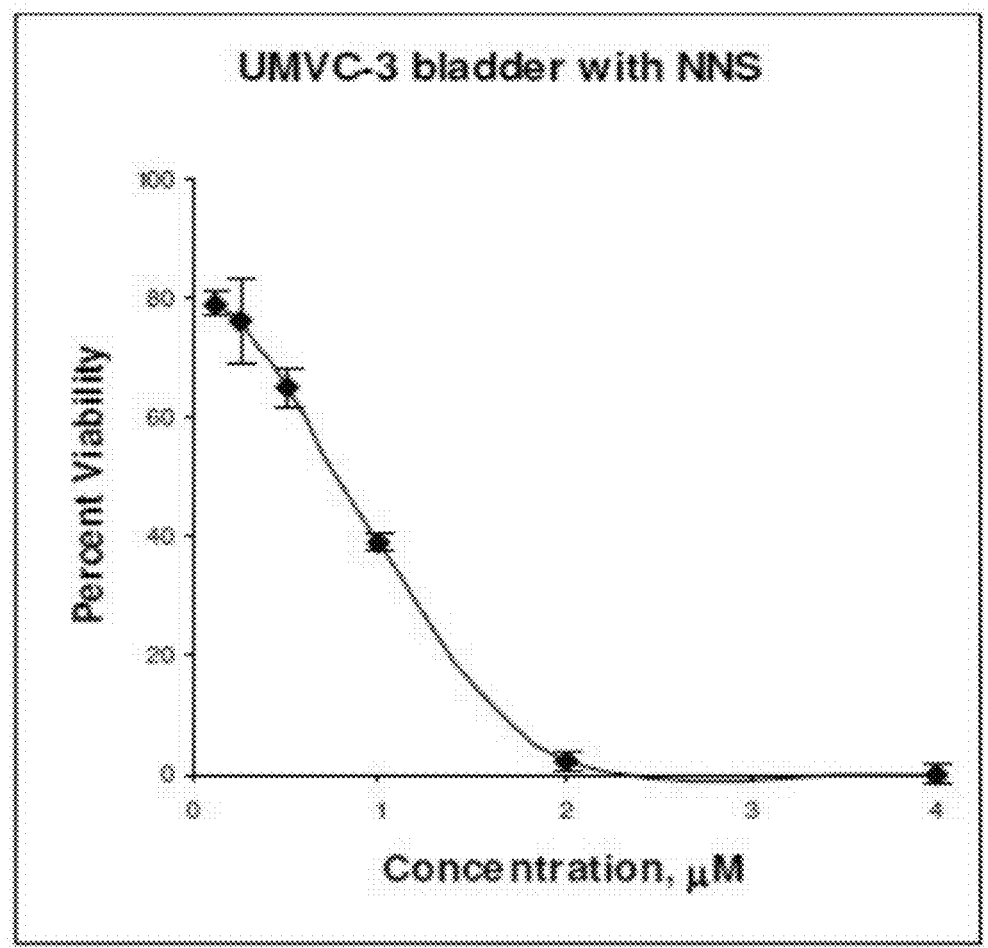
FIG. 9a is a graph for UMVC-3 bladder with CTX-NNS, showing the percent viability for various concentrations.

FIG. 9a is a graph for UMVC-3 bladder with CTX-NNS, showing the percent viability for various concentrations.

Figure 9B:
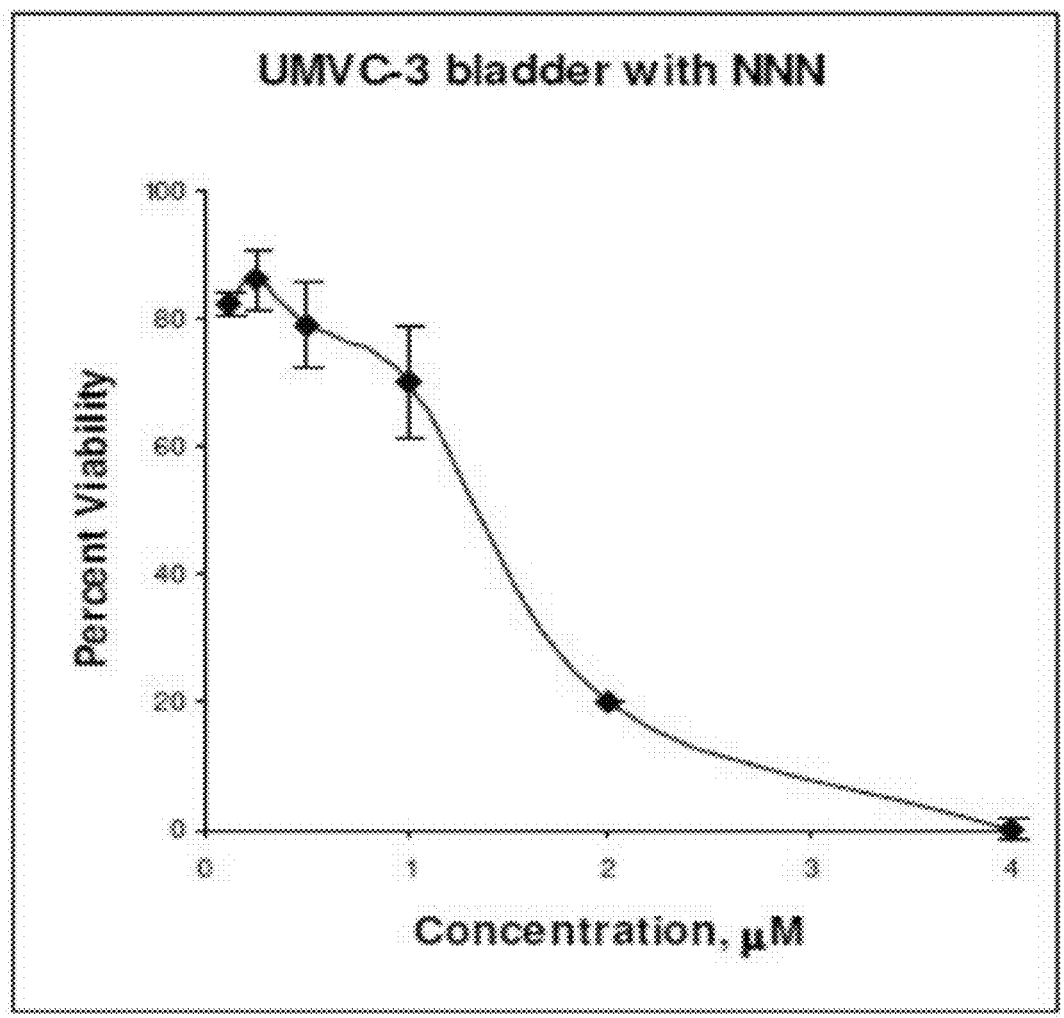
FIG. 9b is a graph for UMVC-3 bladder with CTX-NNN, showing the percent viability for various concentrations.

FIG. 9b is a graph for UMVC-3 bladder with CTX-NNN, showing the percent viability for various concentrations.

Toxicity Studies.

Table 8 provides comparative toxicity data for Ctx-D and a synthetic homologue of lop of NNA CTX-D "L1."

TABLE 8

Comparison of CTx-D and Loop 1 toxicity

| Results (% killing) | LNCaP | DU-145 | R3327 | PC-3 | AY-27 | CEM-2 | CEM-4 |
|---|---|---|---|---|---|---|---|
| CTx-2.5 µM | 100 | 100 | 100 | 97 | 100 | 100 | 011 |
| CTx-1.25 µM | 91 | 94 | 95 | 78 | 71 | 100 | 011 |
| CTx-0.625 µM | 51 | 71 | 60 | 55 | 43 | 92 | 96 |
| *L1-80 µM | 42 | 42 | 23 | 29 | 60 | 4 | 13 |
| L1-40 µM | 29 | 45 | 12 | 26 | 32 | 12 | 12 |
| L1-20 µM | 25 | 23 | 8 | 26 | 4 | 10 | 4 |
| L1-10 µM | 0 | 21 | 0 | 22 | 0 | 22 | 0 |

*synthetic homologue of Loop 1 of NNA CTX-D

Examples of Compositions

In one aspect, the present invention relates to the use of peptide compositions, including in particular, the peptide called L1AD3. The L1AD3 has the sequence: Leu-Lys-Cys-Asn-Lys-Leu-Val-Pro-Leu-Phe-Tyr-Lys-Thr-Cys [single letter code LKCNKLVPLFYKTC], SEQ ID No: 1. This peptide has a disulfide bond between the Cys residues, which occur at positions 3 and 14.

Additional variations of the above peptides can have replacements of at least single amino acid residues. These peptide variations include, but are not limited to:

Leu-Lys-Cys-Asn-Lys-Leu-Ile-Pro-Leu-Phe-Tyr-Lys-Thr-Cys [single letter code: LKCNKLIPLFYKTC] SEQ ID No:2, where, at position 7, Val is replaced by Ile in Seq. ID No. 1.

Leu-Lys-Cys-Asn-Lys-Leu-Ile-Pro-Leu-Ala-Tyr-Lys-Thr-Cys [single letter code: LKCNKLIPLAYKTC] SEQ ID No. 3, where, at position 7, Val is replaced by Ile and at position 10, Phe is replaced by Ala in Seq. ID no. 1.

Leu-Lys-Cys-Asn-Lys-Leu-Val-Pro-Leu-Ala-Tyr-Lys-Thr-Cys [single letter code: LKCNKLVPLAYKTC] SEQ ID No:4, where, at position 10, Phe is replaced by Ala in Seq. ID No. 1.

Leu-Lys-Cys-Gln-Lys-Leu-Val-Pro-Leu-Phe-Tyr-Lys-Thr-Cys [single letter code: LKCQKLVPLFYKTC] SEQ ID No:5, where, at position 4, Asn is replaced by Gln in Seq. ID no. 1.

Other constructs of these peptides, which have the same amino acid composition and sequence as those discussed above, with the exception that these peptides are synthesized with and composed of D-amino acids instead of L-amino acids, because of amino acid alpha carbon chirality. The D-amino acid form of L1AD3 is synthesized sequentially in the opposite direction from that of the L1AD3 peptide (from amino terminus to carboxyl terminus, rather than the conventional COOH to $NH_2$ progression used for synthesizing peptides with L-amino acids) SEQ ID No:6.

The D-amino acid peptides corresponding to the above L-form peptides, and their Seq. ID numbers are as follows:

Cys-Thr-Lys-Tyr-Phe-Leu-Pro-Val-Leu-Lys-Asn-Cys-Lys-Leu [single letter code: CTKYFLPVLKNCKL] SEQ ID No:6, the D-amino acid form of the Seq. ID No. 1.

Cys-Thr-Lys-Tyr-Phe-Leu-Pro-Ile-Leu-Lys-Asn-Cys-Lys-Leu [single letter code: CTKYFLPILKNCKL] SEQ ID No:7, the D-amino acid form of the Seq. ID No. 2.

Cys-Thr-Lys-Tyr-Ala-Leu-Pro-Ile-Leu-Lys-Asn-Cys-Lys-Leu [single letter code: CTKYALPILKNCKL] SEQ ID No:8, the D-amino acid form of the Seq. ID No. 3.

Cys-Thr-Lys-Tyr-Ala-Leu-Pro-Val-Leu-Lys-Asn-Cys-Lys-Leu [single letter code: CTKYALPVLKNCKL] SEQ ID No:9, the D-amino acid form of the Seq. ID No. 4.

Cys-Thr-Lys-Tyr-Phe-Leu-Pro-Val-Leu-Lys-Gln-Cys-Lys-Leu [single letter code: CTKYFLPVLKQCKL] SEQ ID No:10, the D-amino acid form of the Seq. ID No. 5.

Examples of Additional Cobra Toxin Derivatives Include:

*Naja naja atra* cytotoxin-III (CTX), whose sequence is: LKCNKLVPLFYKTCPAGKNLCYKMFM-VATPKVPVKRGCIDVCPKSSLL VKYVCCNTDRCN, SEQ ID No:11.

Biotin-Leu-Lys-Cys-Asn-Lys-Leu-Val-Pro-Leu-Phe-Tyr-Lys-Thr-Cys [single letter code: btn-LKCNKLVPLFYKTC] SEQ ID No:12, where the N-terminal Leu is biotinylated during synthesis of Seq. ID No. 1.

Leu-Lys-Cys-Asn-Lys-Leu-Val-Pro-Leu-Phe-Ser-Lys-Thr-Cys [single letter code: LKCNKLVPLFSKTC] SEQ ID No:13, where, at position 11, Tyr is replaced by Ser in Seq. ID No. 1.

Leu-Lys-Cys-Asn-Lys-Leu-Val-Pro-Leu-Phe-Phe-Lys-Thr-Cys [single letter code: LKCNKLVPLFFKTC] SEQ ID No:14, where, at position 11, Tyr is replaced by Phe in Seq. ID No. 1.

Leu-Lys-Cys-Asn-Lys-Leu-Val-Pro-Leu-Phe-Trp-Lys-Thr-Cys [single letter code: LKCNKLVPLFWKTC] SEQ ID No:15, where, at position 11, Tyr is replaced by Trp in Seq. ID No. 1.

Leu-Lys-Cys-Lys-Lys-Leu-Val-Pro-Leu-Phe-Tyr-Lys-Thr-Cys [single letter code: LKCKKLVPLFYKTC] SEQ ID No:16, where, at position 4, Asn is replaced by Lys in Seq. ID No. 1.

Leu-Lys-Cys-His-Lys-Leu-Val-Pro-Leu-Phe-Tyr-Lys-Thr-Cys [single letter code: LKCHKLVPLFYKTC] SEQ ID No:17, where, at position 4, Asn is replaced by His in Seq. ID No. 1.

Leu-Lys-Cys-Lys-Lys-Leu-Val-Pro-Leu-Phe-Ser-Lys-Thr-Cys [single letter code: LKCKKLVPLFSKTC] SEQ ID No:18, where, at position 4 Asn is replaced by Lys and at position 11, Tyr is replaced by Ser in Seq. ID No. 1.

In certain embodiments; the toxin may be administered in a pharmaceutically acceptable formulation, including, but not limited to: a liquid, a suspension, an emulsion, a powder, a cream, a pill, a troche, a suppository, and a solution. The toxin may be administered by being injected into the prostate in a pharmaceutically acceptable formulation.

In certain embodiments; the toxin may be administered as a single unilateral injection, a series of unilateral injections and/or bilateral injections.

In certain embodiments; the toxin may be administered urethroscopically into the prostate.

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof.

Therefore, it is intended that the invention not be limited to the particular embodiment disclosed herein contemplated for carrying out this invention, but that the invention will include all embodiments falling within the scope of the claims.

Citation of the any of the documents recited herein is not intended as an admission that any of the foregoing is pertinent prior art. All statements as to the date or representation as to the contents of these documents is based on the information available to the applicant and does not constitute any admission as to the correctness of the dates or contents of these documents.

What is claimed is:

1. A method to treat a subject having a non-cancerous hyperplastic prostate disorder, comprising administering to the subject a therapeutically effective amount of an isolated, synthetic or recombinant peptide composition, wherein the peptide composition comprises at least one of the sequences represented by SEQ ID NOS: 1-18, or derivatives thereof, wherein the non-cancerous hyperplastic disorder is alleviated.

2. The method of claim 1, wherein the subject is human.

3. A method for treating prostatic hyperplasia in a subject, comprising administering to the subject a therapeutically effective amount of a composition comprising a cyclic peptide, 14 amino acids in length with a disulfide bond between residues 3 and 14 (Cys 3 and Cys 14) which consists of the following sequence: Leu-Lys-Cys-4-Lys-Leu-7-Pro-Leu-10-Tyr-Lys-Thr-Cys, where 4 is Asn or Gln; 7 is Val or Ile; 10 is Phe or Ala having one or more of the SEQ ID NO:1, SEQ ID NO:2, SEQ ID NO:3, SEQ ID NO:4 and SEQ ID NO:5.

4. A method for treating prostatic hyperplasia in a subject, comprising administering to the subject a therapeutically effective amount of a composition comprising a cyclic peptide, 14 amino acids in length with a disulfide bond between residues 3 and 14 (Cys 3 and Cys 14) which consists of the following sequence: Leu-Lys-Cys-4-Lys-Leu-7-Pro-Leu-10-Tyr-Lys-Thr-Cys, where 4 is Asn or Gln; 7 is Val or Ile; 10 is Phe or Ala, having the SEQ ID NO:1, SEQ ID NO:2, SEQ ID NO:3, SEQ ID NO:4, SEQ ID NO:5, and SEQ ID NO:12, in which at least one amino acid is replaced with its corresponding D-amino acid.

5. A method for treating a subject with a prostatic disorder, the method comprising:
    injecting a therapeutic amount of a composition derived from a cobra toxin thereof into a prostate gland of the subject patient, thereby alleviating a symptom of prostatic hyperplasia, benign prostatic hyperplasia or prostatic enlargement, wherein the composition comprises one or more peptides having a sequence as shown in SEQ ID NOs:1-18.

6. The method of claim 5, wherein the prostatic disorder comprises one or more of: prostatic hyperplasia, benign prostatic hyperplasia or prostatic enlargement.

7. The method of claim 1, wherein the composition is administered in a pharmaceutically acceptable formulation selected from the group consisting of: a liquid, a powder, a cream, an emulsion, a suppository, a suspension, and a solution.

8. The method of claim 5, wherein the composition is administered to the prostate of the patient by a route selected from the group consisting of a single unilateral injection, serial unilateral injections and bilateral injections.

9. The method of claim 5, wherein administration of the composition results in shrinkage of the prostate.

10. The method of claim 1, wherein the composition is conjugated, linked, or bound to a molecule selected from the group consisting of an antibody, antibody fragment, and an antibody-like binding molecule, wherein the molecule has a higher affinity for binding to a tumor or other target than binding to other cells.

11. A system for treating benign prostate hyperplasia (BPH) of a prostate, comprising: administering at least one composition comprising one or more amino acids described in SEQ ID NOs:1-18 near a BPH tissue site of a subject in an amount sufficient to produce necrosis of cells of the BPH tissue site but insufficient to create damage to a majority of the BPH tissue site.

12. A method for treating prostatic hyperplasia in a subject, comprising administering to the subject a therapeutically effective amount of a composition comprising a cyclic peptide, 14 amino acids in length with a disulfide bond between residues 1 and 12 (Cys 1 and Cys 12) which consists of the following sequence: Cys-Thr-Lys-Tyr-5-Leu-Pro-8-Leu-Lys-11-Cys-Lys-Leu, where 5 is Phe or Ala; 8 is Val or Ile; 11 is Asn or Gln having one or more of the SEQ ID NO:6, SEQ ID NO:7, SEQ ID NO:8, SEQ ID NO:9 and SEQ ID NO:10.

13. A method for treating prostatic hyperplasia in a subject, comprising administering to the subject a therapeutically effective amount of a composition comprising a peptide, 14 amino acids in length having SEQ ID NO:11.

14. A method for treating prostatic hyperplasia in a subject, comprising administering to the subject a therapeutically effective amount of a composition comprising a peptide, 14 amino acids in length having SEQ ID NO:12.

* * * * *

SEQUENCE LISTING

```
<160> NUMBER OF SEQ ID NOS: 21

<210> SEQ ID NO 1
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (3)..(14)

<400> SEQUENCE: 1

Leu Lys Cys Asn Lys Leu Val Pro Leu Phe Tyr Lys Thr Cys
1               5                   10

<210> SEQ ID NO 2
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: DISULFID
<222> LOCATION: (3)..(14)

<400> SEQUENCE: 2

Leu Lys Cys Asn Lys Leu Ile Pro Leu Phe Tyr Lys Thr Cys
1               5                   10

<210> SEQ ID NO 3
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (3)..(14)

<400> SEQUENCE: 3

Leu Lys Cys Asn Lys Leu Ile Pro Leu Ala Tyr Lys Thr Cys
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (3)..(14)

<400> SEQUENCE: 4

Leu Lys Cys Asn Lys Leu Val Pro Leu Ala Tyr Lys Thr Cys
1               5                   10

<210> SEQ ID NO 5
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (3)..(14)

<400> SEQUENCE: 5

Leu Lys Cys Gln Lys Leu Val Pro Leu Phe Tyr Lys Thr Cys
1               5                   10

<210> SEQ ID NO 6
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (1)..(12)
<220> FEATURE:
<221> NAME/KEY: MOD_RES
<222> LOCATION: (1)..(14)
<223> OTHER INFORMATION: D-amino acids

<400> SEQUENCE: 6

Cys Thr Lys Tyr Phe Leu Pro Val Leu Lys Asn Cys Lys Leu
1               5                   10
```

```
<210> SEQ ID NO 7
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (1)..(12)
<220> FEATURE:
<221> NAME/KEY: MOD_RES
<222> LOCATION: (1)..(14)
<223> OTHER INFORMATION: D-amino acids

<400> SEQUENCE: 7

Cys Thr Lys Tyr Phe Leu Pro Ile Leu Lys Asn Cys Lys Leu
1               5                   10

<210> SEQ ID NO 8
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (1)..(12)
<220> FEATURE:
<221> NAME/KEY: MOD_RES
<222> LOCATION: (1)..(14)
<223> OTHER INFORMATION: D-amino acids

<400> SEQUENCE: 8

Cys Thr Lys Tyr Ala Leu Pro Ile Leu Lys Asn Cys Lys Leu
1               5                   10

<210> SEQ ID NO 9
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (1)..(12)
<220> FEATURE:
<221> NAME/KEY: MOD_RES
<222> LOCATION: (1)..(14)
<223> OTHER INFORMATION: D-amino acids

<400> SEQUENCE: 9

Cys Thr Lys Tyr Ala Leu Pro Val Leu Lys Asn Cys Lys Leu
1               5                   10

<210> SEQ ID NO 10
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (1)..(12)
<220> FEATURE:
<221> NAME/KEY: MOD_RES
<222> LOCATION: (1)..(14)
<223> OTHER INFORMATION: D-amino acids

<400> SEQUENCE: 10
```

```
Cys Thr Lys Tyr Phe Leu Pro Val Leu Lys Gln Cys Lys Leu
1               5                   10

<210> SEQ ID NO 11
<211> LENGTH: 60
<212> TYPE: PRT
<213> ORGANISM: Naja atra

<400> SEQUENCE: 11

Leu Lys Cys Asn Lys Leu Val Pro Leu Phe Tyr Lys Thr Cys Pro Ala
1               5                   10                  15

Gly Lys Asn Leu Cys Tyr Lys Met Phe Met Val Ala Thr Pro Lys Val
            20                  25                  30

Pro Val Lys Arg Gly Cys Ile Asp Val Cys Pro Lys Ser Ser Leu Leu
        35                  40                  45

Val Lys Tyr Val Cys Cys Asn Thr Asp Arg Cys Asn
    50                  55                  60

<210> SEQ ID NO 12
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Biotin-Leu

<400> SEQUENCE: 12

Leu Lys Cys Asn Lys Leu Val Pro Leu Phe Tyr Lys Thr Cys
1               5                   10

<210> SEQ ID NO 13
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (3)..(14)

<400> SEQUENCE: 13

Leu Lys Cys Asn Lys Leu Val Pro Leu Phe Ser Lys Thr Cys
1               5                   10

<210> SEQ ID NO 14
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (3)..(14)

<400> SEQUENCE: 14

Leu Lys Cys Asn Lys Leu Val Pro Leu Phe Phe Lys Thr Cys
1               5                   10

<210> SEQ ID NO 15
<211> LENGTH: 14
<212> TYPE: PRT
```

-continued

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (3)..(14)

<400> SEQUENCE: 15

Leu Lys Cys Asn Lys Leu Val Pro Leu Phe Trp Lys Thr Cys
1               5                   10

<210> SEQ ID NO 16
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (3)..(14)

<400> SEQUENCE: 16

Leu Lys Cys Lys Lys Leu Val Pro Leu Phe Tyr Lys Thr Cys
1               5                   10

<210> SEQ ID NO 17
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (3)..(14)

<400> SEQUENCE: 17

Leu Lys Cys His Lys Leu Val Pro Leu Phe Tyr Lys Thr Cys
1               5                   10

<210> SEQ ID NO 18
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (3)..(14)

<400> SEQUENCE: 18

Leu Lys Cys Lys Lys Leu Val Pro Leu Phe Ser Lys Thr Cys
1               5                   10

<210> SEQ ID NO 19
<211> LENGTH: 15
<212> TYPE: PRT
<213> ORGANISM: Naja kaouthia

<400> SEQUENCE: 19

Met Glu Cys Tyr Arg Met Ser Asn Ile Val Thr Cys Gln Pro Trp
1               5                   10                  15

<210> SEQ ID NO 20
<211> LENGTH: 14
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: DISULFID
<222> LOCATION: (3)..(14)
<220> FEATURE:
<221> NAME/KEY: MOD_RES
<222> LOCATION: (4)..(4)
<223> OTHER INFORMATION: Asn or Gln
<220> FEATURE:
<221> NAME/KEY: MOD_RES
<222> LOCATION: (7)..(7)
<223> OTHER INFORMATION: Val or Ile
<220> FEATURE:
<221> NAME/KEY: MOD_RES
<222> LOCATION: (10)..(10)
<223> OTHER INFORMATION: Phe or Ala

<400> SEQUENCE: 20

Leu Lys Cys Xaa Lys Leu Xaa Pro Leu Xaa Tyr Lys Thr Cys
1               5                   10

<210> SEQ ID NO 21
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (3)..(14)
<220> FEATURE:
<221> NAME/KEY: MOD_RES
<222> LOCATION: (4)..(4)
<223> OTHER INFORMATION: Asn or Gln
<220> FEATURE:
<221> NAME/KEY: MOD_RES
<222> LOCATION: (7)..(7)
<223> OTHER INFORMATION: Val or Ile
<220> FEATURE:
<221> NAME/KEY: MOD_RES
<222> LOCATION: (10)..(10)
<223> OTHER INFORMATION: Phe or Ala

<400> SEQUENCE: 21

Leu Lys Cys Xaa Lys Leu Xaa Pro Leu Xaa Tyr Lys Thr Cys
1               5                   10
```